United States Patent
Haruta et al.

[11] Patent Number: 5,214,056
[45] Date of Patent: May 25, 1993

[54] 1,3,2-DIOXATHIOLANE OXIDE DERIVATIVE

[75] Inventors: Jun-ichi Haruta; Masahiro Tanaka; Itsuo Uchida, all of Yokohama; Akira Ohta; Shin Hara, both of Hadano, all of Japan

[73] Assignee: Japan Tobacco Inc., Tokyo, Japan

[21] Appl. No.: 752,622

[22] PCT Filed: Dec. 26, 1990

[86] PCT No.: PCT/JP90/01704
§ 371 Date: Aug. 20, 1991
§ 102(e) Date: Aug. 20, 1991

[87] PCT Pub. No.: WO91/09851
PCT Pub. Date: Jul. 11, 1991

[30] Foreign Application Priority Data

Dec. 27, 1989 [JP] Japan .................................. 1-336247
Aug. 13, 1990 [JP] Japan .................................. 2-211682

[51] Int. Cl.$^5$ .................. A61K 31/39; A61K 31/445; C07D 327/10; C07D 211/26
[52] U.S. Cl. ..................................... 514/326; 514/422; 514/439; 514/551; 514/563; 546/209; 546/226; 546/247; 548/517; 548/527; 548/540; 560/1; 560/41; 560/121; 560/423; 560/125; 560/126; 560/169; 562/437; 562/432; 562/560; 562/503; 562/505; 562/507; 562/564; 562/508; 549/34; 549/449; 549/452
[58] Field of Search ..................... 549/34, 452, 449; 560/41, 169, 123, 124, 121, 125, 126, 1; 562/432, 560, 563, 505, 507, 564, 437, 508; 514/439, 467, 551, 563, 422, 366; 546/207, 226, 247; 548/527, 517, 540

[56] References Cited

U.S. PATENT DOCUMENTS 4,333,879 6/1982 Tamai et al. ........................ 549/549
4,382,889 5/1983 Tamai et al. ........................ 549/549
5,023,342 6/1991 Sharpless et al. ...................... 549/34

FOREIGN PATENT DOCUMENTS 52-23021 2/1977 Japan .
55-115878 9/1980 Japan .
59-7186 1/1984 Japan .
61-227588 10/1986 Japan .
64-5031 1/1989 Japan .

OTHER PUBLICATIONS

Chemical Abstracts 101: 7167x, p. 613, abstract of J.P. 59-07,186 [84-07,186] (1984).
T. Seki, Chemical Abstracts 87: 202,125b, p. 784, abstract of 52-23021 (1977).
O. Kawabata, et al. Chemical Abstracts, 106: 176,398g, p. 731, abstract of JP-61-227,578 [86-277,578] (1987).

Primary Examiner—Richard L. Raymond
Assistant Examiner—Mark W. Russell
Attorney, Agent, or Firm—Birch, Stewart, Kolasch & Birch

[57] ABSTRACT

A 1,3,2-dioxathiolane oxide derivative is represented by the following formula:

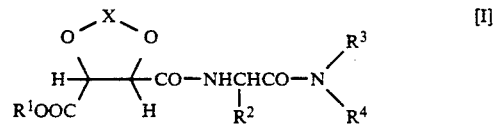

wherein
X represents —S(O)— or —S(O)$_2$—;
R$^1$ represents a hydrogen atom, an alkali metal atom, a benzyl group, or a lower alkyl group;
R$^2$ represents a lower alkyl group which may be substituted with a methylthio group, or a benzyl group, and
R$^3$ and R$^4$ may be the same or different and independently represent a hydrogen atom, an alkyl group having one to ten carbon atoms, a lower alkyl group substituted with a guanidyl group, a cycloalkyl group having 3 to 6 carbon atoms, a phenyl group, a benzyl group, or a phenethyl group, or together form an alkylene group.

23 Claims, No Drawings

1,3,2-DIOXATHIOLANE OXIDE DERIVATIVE

TECHNICAL FIELD

The present invention relates to a novel 1,3,2-dioxathiolane oxide derivative and its intermediate compound. More particularly, the present invention relates to a novel 1,3,2-dioxathiolane oxide derivative having good inhibitory activity against thiol proteases such as calcium-dependent neutral protease (CANP) and cathepsins B, H, and L, and also relates to a 1,3-dioxolane derivative and a 1,2-diol derivative useful to prepare the 1,3,2-dioxathiolane derivative.

BACKGROUND ART

Proteolytic enzymes represented by CANP and including, e.g., cathepsin B, papain, ficin, bromelin, and bromelan are generally called thiol proteases because they have a thiol group at the active center. On the other hand, it is known that substances having CANP inhibition activity not only specifically affect the thiol group of the CANP to inhibit its activity but also have an inhibitory effect on other thiol proteases.

Therefore, substances capable of inhibiting proteases such as CANP and cathepsin B are expected to useful the cure, mitigation, treatment, or prevention of diseases to which these proteases are related, e.g., myotonic dystrophy, inflammation, renal hypertension, cataract, myocardial infarct, viral infectious diseases, malignant tumors, osteoporosis, and allergic diseases.

Conventionally known examples of a compound having thiol protease inhibition activity are E-64, a mold metabolite, a series of epoxy succinic acid derivatives such as E-64-c as derivatives of E-64, and aldehyde derivatives of leupeptin and antipine belonging to a secondary metabolite of an actinomycete.

E-64 is an epoxysuccinic acid derivative obtained from a bran solid culture of an *Aspergillus japonicus* TPR-64 strain and represented by the following formula (e.g., Published Unexamined Japanese Patent Application No. 52-23021 and Published Examined Japanese Patent Application No. 64-5031):

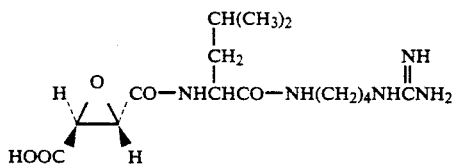

Both E-64-c and loxistatin as its ethylester are derivatives of the above E-64 and are represented by the following formula (e.g., Published Unexamined Japanese Patent Application No. 55-115878):

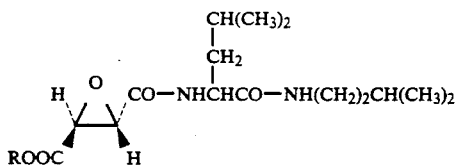

R = H; E-64-c
R = C₂H₅; loxistatin

The above two compounds, especially loxistatin, have attracted attention due to their effect as proteolytic enzyme inhibitors, and are therefore currently being studied to develop a practical use therefor an agent for treating muscular dystrophy and the like.

DISCLOSURE OF INVENTION

It is an object of the present invention to provide a novel compound effective in the cure, mitigation, treatment, or prevention of diseases as described above. The present inventors have conducted extensive studies to achieve this object, and have found that a novel 1,3,2-dioxathiolane oxide derivative has high specific inhibitory activity against thiol proteases, and established the present invention.

The novel 1,3,2-dioxathiolane oxide derivative according to the present invention is represented by the following formula [I]:

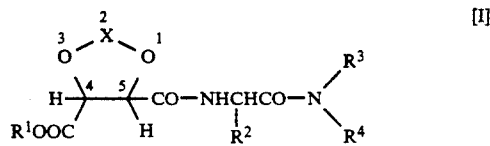

wherein

X represents —S(O)— or —S(O)₂—;

$R^1$ represents a hydrogen atom, an alkali metal atom, a benzyl group, or a lower alkyl group;

$R^2$ represents a lower alkyl group which may be substituted with a methylthio group, or a benzyl group; and $R^3$ and $R^4$ may be the same or different, and independently represent a hydrogen atom, an alkyl group having one to ten carbon atoms, a lower alkyl group substituted with a guanidyl group, a cycloalkyl group having 3 to 6 carbon atoms, a phenyl group, a benzyl group, or a phenethyl group, or together form an alkylene group.

The lower alkyl group represented by $R^1$ and $R^2$ represents a straight-chain or branched alkyl group having one to five, and preferably, one to four carbon atoms. Examples of this alkyl group are a methyl group, an ethyl group, a propyl group, an isopropyl group, a butyl group, a sec-butyl group, and a tert-butyl group etc.

The alkyl group represented by $R^3$ and $R^4$ represents a straight-chain or branched alkyl group having one to ten carbon atoms. Examples of this alkyl group are a methyl group, an ethyl group, a propyl group, an isopropyl group, a butyl group, a sec-butyl group, a tert-butyl group, a pentyl group, an isopentyl group, a hexyl group, an isohexyl group, a heptyl group, an isoheptyl group, an octyl group, an isooctyl group, a nonyl group, an isononyl group, a decyl group, and an isodecyl group. The alkylene group represents a divalent group derived from a saturated straight-chain aliphatic hydrocarbon having two to five carbon atoms.

Another object of the present invention is to provide an intermediate compound useful in preparing the above 1,3,2-dioxathiolane oxide derivative [I]. This object is achieved via a 1,2-diol derivative [II] and a 1,3-dioxolane derivative [III] represented by the following formulas:

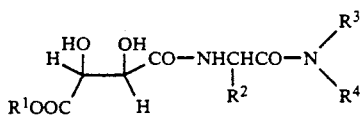           [II]

wherein $R^1$, $R^2$, $R^3$, and $R^4$ are each the same as defined in the above formula [I], and

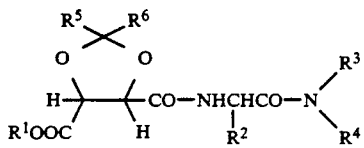           [III]

wherein
$R^1$, $R^2$, $R^3$, and $R^4$ are each the same as defined in the above formula [I]; and
$R^5$ and $R^6$ may be the same or different and independently represent a hydrogen atom, a lower alkyl group, a substituted or nonsubstituted phenyl group, a lower alkoxy group, or a lower alkylamino group.

In comparison with the conventional epoxy succinic acid derivatives described above, the most important characteristic of the novel 1,3,2-dioxathiolane oxide derivative [I] according to the present invention lies in the fact that the heterocyclic moiety of the derivative is not a substituted epoxy ring but a substituted 1,3,2-dioxathiolane oxide ring. On the basis of this characteristic, the novel compound [I] of the present invention achieves a thiol protease inhibitory effect better than those obtained by conventionally known substances having similar inhibitory activity.

Methods of preparing the 1,3,2-dioxathiolane oxide derivative [I] of the present invention will be described below. However, the methods to be described below are merely examples. Therefore, the compound [I] can be prepared by methods other than these exemplified methods. The following methods include methods of preparing the intermediate compounds [II] and [III] of the present invention. As is the case with the above compound, these intermediate compounds can be prepared by methods other than the exemplified methods.

Preparing method 1

Preparation of 1,3-dioxolane derivative [III]

Method A

An amino acid derivative represented by the following formula [IV] or its reactive derivative

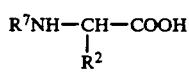           [IV]

(wherein $R^7$ represents a protective group of an amino group such as a tert-butoxycarbonyl group and $R^2$ has the same meaning as defined above) and an amine derivative represented by the following formula [V] or its salt are condensed,

           [V]

(wherein $R^3$ and $R^4$ have the same meanings as defined above) thereby obtaining a compound represented by the following formula [VI]:

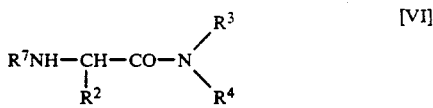           [VI]

(wherein $R^2$, $R^3$, $R^4$, and $R^7$ have the same meanings as defined above.)

Subsequently, the protective group $R^7$ of the compound [VI] was removed in accordance with a conventional method to obtain an amide derivative represented by the following formula [VII]:

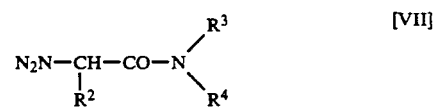           [VII]

(wherein $R^2$, $R^3$, and $R^4$ have the same meanings as defined above.)

Thereafter, this amide derivative [VII] or its reactive derivative and a tartarate monoester derivative synthesized in accordance with a method by A. Tanaka et al. [*Agric. Biol. Chem.*, 48, 2135 (1984)] and represented by the following formula [VIII] or its reactive derivative are condensed,

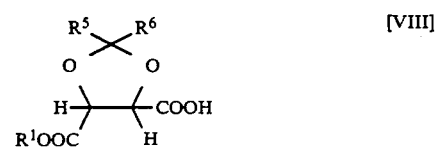           [VIII]

(wherein $R^1$, $R^5$, and $R^6$ have the same meanings as defined above) thereby obtaining a 1,3-dioxolane derivative represented by the following formula [III]:

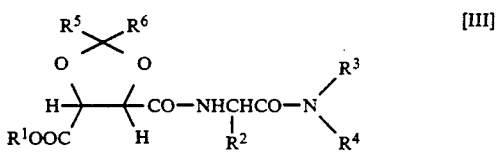           [III]

(wherein $R^1$, $R^2$, $R^3$, $R^4$, $R^5$, and $R^6$ have the same meanings as defined above.)

Method B

A tartarate monoester derivative represented by the above formula [VIII] or its reactive derivative and an amine derivative represented by the following formula [IX] or its salt are condensed,

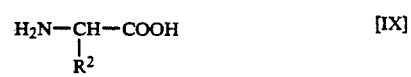           [IX]

(wherein $R^2$ has the same meaning as defined above) thereby obtaining an amidocarboxylic acid derivative represented by the following formula [X] or its reactive derivative:

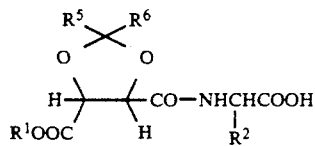

(wherein $R^1$, $R^2$, $R^5$, and $R^6$ have the same meanings as defined above.)

Subsequently, the amidocarboxylic acid derivative [X] or its reactive derivative and an amine derivative represented by the above formula [V] or its salt are condensed, thereby obtaining a 1,3-dioxolane derivative represented by the formula [III].

Preparing method 2

Preparation of 1,2-diol derivative [II]

Method C

A 1,2-diol derivative represented by the following formula [II]

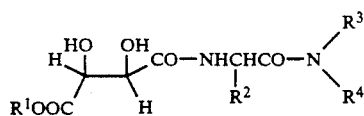

(wherein $R^1$, $R^2$, $R^3$, and $R^4$ have the same meanings as defined above) is obtained by subjecting a 1,3-dioxolane derivative represented by the following formula [III] to a reduction process such as catalytic reduction or performing an acid treatment for the derivative:

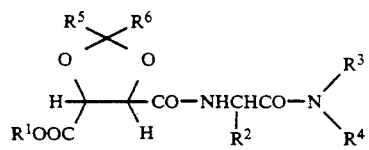

(wherein $R^1$, $R^2$, $R^3$, $R^4$, $R^5$, and $R^6$ have the same meanings as defined above.)

Preparing method 3

Preparation of 1,3,2-dioxathiolane oxide derivative [I]

Method D

Of the 1,3,2-dioxathiolane oxide derivatives represented by the formula [I],

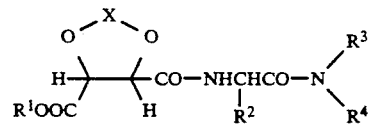

(wherein $R^1$, $R^2$, $R^3$, $R^4$, and X have the same meanings as defined above) a 1,3,2-dioxathiolane-2-oxide derivative in which X is —S(O)— can be manufactured as follows.

That is, by employing a method by K. B. Sharpless et al. [*J. Am. Chem. Soc.*, 110, 7538 (1988)] for a 1,2-diol derivative represented by the formula [II],

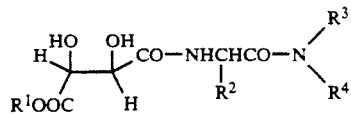

(wherein $R^1$, $R^2$, $R^3$, and $R^4$ have the same meanings as defined above) a 1,3,2-dioxathiolane-2-oxide derivative represented by the following formula [XI] can be obtained:

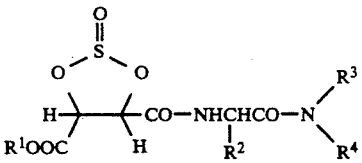

(wherein $R^1$, $R^2$, $R^3$, and $R^4$ have the same meanings as defined above.)

In addition, by oxidizing this 1,3,2-dioxathiolane 2-oxide derivative [XI], the compound [I] in which X is —S(O)$_2$—, i.e., a 1,3,2-dioxathiolane-2,2-dioxide derivative represented by the following formula [XII] can be obtained:

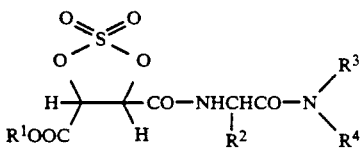

(wherein $R^1$, $R^2$, $R^3$, and $R^4$ have the same meanings as defined above.)

Note that the compound [II] may be prepared in accordance with the following method.

First, tartaric anhydride is produced from tartaric acid in accordance with a method by M. J. Miller et al., (*J. Org. Chem.*, 47, 4928 (1982)], and $R^1OH$ (wherein $R^1$ has the same meaning as defined above) is reacted with the tartaric anhydride without isolating the anhydride, thereby obtaining tartrate monoester represented by the following formula [XIII]:

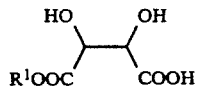

(wherein $R^1$ has the same meaning as defined above.)

Subsequently, the monoester [XIII] or its reactive derivative and the above compound [VII] or its salt are condensed to obtain a 1,2-diol derivative represented by the formula [II].

In the above preparation methods, the starting compounds [V], [VII], and [IX] may be used either in the free state or in the form of a salt. A preferable example of the salt is an acid salt. Examples of the acid salt are an acid salt with an inorganic acid such as hydrochloric acid, sulfuric acid, phosphoric acid, or hydrobromic acid, and an acid salt with an organic acid such as trifluoroacetic acid, p-toluenesulfonic acid, tartaric acid, maleic acid, fumaric acid, or succinic acid.

As reactive derivatives of the compounds [IV], [VIII], and [X], active esters (e.g., N-hydroxysuccinimido ester, pentachlorophenyl ester, N-hydroxybenzotriazole ester) corresponding to the respective compounds, an acid halide (e.g., acid chloride), acid azide, a mixed acid anhydride, and imidazole amide and the like can be used. The active ester may be isolated and subjected to the condensation reaction or subjected to the condensation reaction in situ without being isolated.

As the protective group ($R^7$) in the compounds [IV] and [VI], any protective group normally used in peptide synthesis can be used. Preferable examples of the protective group are a tert-butoxycarbonyl group, a benzyloxycarbonyl group, a benzyl group, a tosyl group, a 2,4-dinitrophenyl group and the like.

Reaction conditions and the like of the respective reactions used in the above preparing methods will be described in detail below.

Preparing method 1: Methods A & B

The condensation reaction between the compound [IV] or its reactive derivative and the compound [V] or its salt; the condensation reaction between the compound [VII] or its salt and the compound [VIII] or its reactive derivative; the condensation reaction between the compound [IX] or its salt and the compound [VIII] or its reactive derivative; and the condensation reaction between the compound [X] or its reactive derivative and the compound [V] or its salt can be performed in accordance with a known peptide reaction in the presence of a condensation agent.

Preferable examples of the condensation agent are dicyclohexylcarbodiimide, 1-ethyl-3-(3-dimethylaminopropyl)carbodiimide hydrochloride, phosphorus oxychloride, phosphorus trichloride, thionyl chloride, oxalyl chloride, triphenylphosphine, and a Vilsmeyer's reagent.

The condensation reaction is preferably performed at a temperature of $-50°$ C. to $50°$ C. by preferably selecting dimethylformamide, methylene chloride, dioxane, tetrahydrofuran, acetonitrile, ethyl acetate, pyridine, acetone, and water as a reaction solvent.

In order to perform the condensation reaction by using salts of the compounds [V], [VII], and [IX], the condensation reaction is performed in the presence of a deoxidizer. Examples of the deoxidizer are trialkylamine (e.g., triethylamine and trimethylamine), N,N-dialkylaniline (e.g., N,N-dimethylaniline and N,N-diethylaniline), pyridine, N-alkylmorpholine (e.g., N-methylmorpholine), an alkali metal hydroxide (e.g., potassium hydroxide and sodium hydroxide), an alkali metal carbonate (e.g., potassium carbonate), and an alkali metal hydrogen carbonate (e.g., sodium hydrogen carbonate).

Removal of the protective group ($R^7$) of the compound [VI] can be easily performed by a conventional method depending on the type of a protective group. For example, catalytic reduction, electrolytic reduction, an acid treatment, an oxidation reaction, or the like may be used.

Preparing method 2: Method C

The reaction of removing cyclic acetal of the compound [III] to produce the compound [II] can be performed by using conditions normally used to remove acetal. For example, the reaction can be performed by means of catalytic reduction or using an inorganic acid such as sulfuric acid and hydrochloric acid, an organic acid such as acetic acid and tosyl acid, or a Lewis acid such as boron trichloride.

Preparing method 3: Method D

The oxidation reaction from the compound [XI] to the compound [XII] can be performed by using a method normally used to perform oxidation from a sulfoxide to a sulfone. For example, a permanganate, a chromate, a peroxide, and a ruthenium trichloride-periodate can be used.

A compound represented by formula [I] in which $R^1$ is a hydrogen atom, i.e., a compound represented by the following formula [XIV] can be easily obtained from a corresponding ester compound [I]:

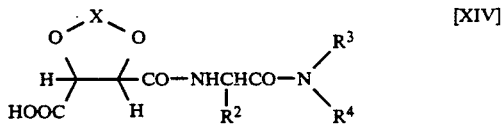

As a method for this purpose, a method normally performed to convert an ester into a corresponding carboxylic acid, e.g., acid hydrolysis, alkali hydrolysis, or catalytic reduction can be used. A compound represented by formula [XIV] obtained in this manner can be converted into a salt of an alkali metal such as Na or K by a conventional method.

In the above reactions, each of the starting compounds [IV] to [X], the intermediate products [II] and [III], and the target compound [I] have one to four asymmetric carbon atoms. In addition, each of the above reactions can be performed without causing racemization. Therefore, when the starting compounds [IV] to [X] are optically active, their intermediate products and the target compound can also be obtained as optically active compounds. However, the above preparing methods can be performed not using optically active compounds [IV] to [X] but using a racemic mixture thereof as starting materials.

A target compound of the present invention represented by formula [I] and prepared by the above methods can form pharmacologically acceptable salts. Examples of the salts are an acid salt with an inorganic acid such as hydrochloric acid, sulfuric acid, phosphoric acid, and hydrobromic acid, and an acid salt with an organic acid such as tartaric acid, maleic acid, fumaric acid, succinic acid, and sulfonic acid.

When the 1,3,2-dioxathiolane oxide derivative [I] according to the present invention or its salt is to be used as a medical preparation, the derivative or its salt can be administered to a patient by using a proper administrable form containing the derivative or its salt as an active component via administration either orally or parenterally. Examples of an orally administrable form are a tablet, a capsule, a granule, a powder, and a liquid preparation. Examples of a parenteral administrable form are an injection preparation, a suppository, an ointment, and a liquid preparation. To obtain these various types of preparations, an excipient, a stabilizer, a preservative agent, a buffer agent, and other additives can be arbitrarily, selectively used in accordance with conventional methods in this field of art. The dose of the preparation is adjustable in accordance with the age, sex, weight, and degree of symptoms of a patient and the administration method. Normally, the dose of the compound of the present invention is set from 10 mg to 1 g/day for an adult per day, but it is not limited to this value.

Test examples performed for the novel compound of the present invention to check the inhibitory effect against thiol proteases will be described below.

TEST EXAMPLE I (1) CANP inhibition activity in in vitro system

A solution mixture consisting of the following components was prepared.

A 167-mM Tris hydrochloric acid buffer solution (pH=7.4) (containing 15-mM mercaptoethanol); 40 μl A solution obtained by dissolving the compound [I] of the present invention in the same Tris hydrochloric acid buffer solution as described above; 40 μl Purified calpain [obtained by a method described in *J. Biol. Chem.*, 239, 149 (1964)] sampled from a rat brain and dissolved in a 50-mM sodium acetic acid buffer solution (pH=6.0; containing 1-mM EDTA and 5-mM mercaptoethanol) 11 units/ml; 200 μl An N,N-dimethylcasein solution (pH=7.0) (25 mg/ml); 80 μl 40 μl of a 167-mM Tris hydrochloric acid buffer solution (pH=7.4) containing 50-mM $CaCl_2$ were added to the above solution mixture, and the resultant solution was incubated at 30° C. for 20 minutes. After the incubation, 320 μl of 10% (W/V) trichloroacetic acid were added to stop the reaction, and the resultant solution was left to stand in an ice bath for one hour. Thereafter, the solution was subjected to centrifugal separation (16,100×g, five minutes), and 600 μl of the supernatant were sampled to measure absorbance ($a_1$) at 280 nm.

In another step, absorbance ($a_2$) was obtained by performing an experiment and measurement following the same procedures as described above except that a 167-mM Tris hydrochloric acid buffer solution (pH=7.4; containing 15-mM mercaptoethanol) was used in place of the 167-mM Tris hydrochloric acid buffer solution containing the compound of the present invention. In addition, absorbance ($a_3$) was obtained by performing an experiment and measurement following the same procedures as described above except that a 167-mM Tris hydrochloric acid buffer solution (pH=7.4; containing 1-mM EDTA) was used in place of the 167-mM tris buffer solution (pH=7.4) containing 50-mM $CaCl_2$.

An inhibition ratio was calculated from the above absorbance values ($a_1$), ($a_2$), and ($a_3$) in accordance with the following equation:

$$\text{Inhibition ratio (\%)} = \left[ 1 - \frac{a_1 - a_3}{a_2 - a_3} \right] \times 100$$

In addition, a concentration (IC50) required for 50% inhibition was calculated by using a semilogarithmical graph. The results are summarized in Table 1 below.

TABLE 1

| Example No. of compound | 50% inhibition concentration $IC_{50}$ (μM) |
|---|---|
| Example 4 | 15 |
| Example 11 | 6.0 |
| Example 12 | 0.3 |
| E-64 | 7.0 |

(2) Cathepsin B inhibition activity in in-vitro system

In this experiment, a 100-mM sodium phosphate buffer solution (pH=6.0; containing 1.33-mM EDTA $Na_2$) was used as the buffer solutions for solution preparation.

A solution mixture consisting of the following components was prepared.

The above buffer solution; 850 μl

A 20-μM solution obtained by dissolving the compound of the present invention in the above buffer solution; 50 μl A solution obtained by dissolving cathepsin B (available from Sigma Co.) in the above buffer solution to have a concentration of 0.5 mg/ml; 50 μl 50 μl of a 200-μM solution obtained by dissolving benzoyl-(phenylalanyl-alginyl)-4-methyl-coumarinamide in the above buffer solution were added to the above solution mixture, and the resultant solution was incubated at 30° C. for 20 minutes.

After the incubation, the reaction solution mixture was cooled in an ice bath to stop the reaction. After 20 minutes elapsed, the fluorescence intensity ($b_1$) at an excitation wavelength of 370 nm and an emission wavelength of 440 nm was measured. At the same time, an experiment was performed using the above buffer solution in place of the solution of cathepsin B in the above system, and fluorescence intensity ($b_2$) was measured following the same procedures as described above. In addition, an experiment was performed using the above buffer solution in place of the buffer solution of the compound of the present invention, and fluorescence intensity ($b_3$) was measured following the same procedures as described above.

An inhibition ratio was calculated in accordance with the following equation:

$$\text{Inhibition ratio (\%)} = \left[ 1 - \frac{b_1 - b_2}{b_3 - b_2} \right] \times 100$$

and a concentration ($IC_{50}$) required for 50% inhibition was calculated by using a semilogarithmical graph. The results are summarized in Table 2 below.

TABLE 2

| Example No. of compound | 50% inhibition concentration $IC_{50}$ (μM) |
|---|---|
| Example 4 | 0.025 |
| Example 11 | 0.009 |
| Example 12 | 0.0007 |
| Example 14 | 0.015 |
| Example 16 | 0.003 |
| E-64 | 0.035 |

TEST EXAMPLE II

The following test was performed to confirm that the compound of the present invention had no adverse effect on activity of a proteolytic enzyme such as trypsin, chymotrypsin, elastase, and leucine-aminopeptidase.

(1) Effect on trypsin

In this experiment, a 50-mM Tris hydrochloric acid buffer solution (pH=8.0) was used as the buffer solutions for solution preparation.

A solution mixture consisting of the following components was prepared.

The above buffer solution; 850 μl

A 20-μM solution obtained by dissolving the compound of the present invention in the above buffer solution; 50 μl A solution obtained by dissolving trypsin (available from Sigma Co.) in the above buffer solution to have a concentration of 0.5 mg/ml; 50 μl 50 μl of a 200-μM solution obtained by dissolving 7-(prolyl-phenylalanyl-alginyl)-4-methyl-coumarinamide in the above buffer solution was added to the above solution mixture, and the resultant solution was incubated at 30° C. for 20 minutes.

After the incubation, the reaction solution mixture was poured in an ice bath to stop the reaction. After 20 minutes elapsed, the fluorescence intensity ($c_1$) at an excitation wavelength of 370 nm and an emission wavelength of 440 nm was measured. At the same time, experiments were performed using the above buffer solution in place of the trypsin solution and in place of the buffer solution of the compound of the present invention in the above system, thereby measuring fluorescence intensities ($c_2$) and ($c_3$) following the same procedures as described above, respectively.

When an inhibition ratio was calculated in accordance with the following equation, the inhibition ratio was 0%.

$$\text{Inhibition ratio (\%)} = \left[1 - \frac{c_1 - c_2}{c_3 - c_2}\right] \times 100$$

This result indicates that each compound of the present invention described in Table 2 does not inhibit trypsin under the above conditions.

Similarly, when a test was performed to check the inhibition activity of the compound of the present invention against chymotrypsin, elastase, and leucine-aminopeptidase, the inhibition ratio for each enzyme was 0%.

BEST MODE OF CARRYING OUT THE INVENTION

The present invention will be described in more detail below by way of its references examples and working examples, but the present invention is not limited to these examples. For example, the following compounds also belong to the present invention.

Ethyl (4S,5S)-5-[(S)-1-decylcarbamoyl-3-methylbutylcarbamoyl]-1,3,2-dioxathiolane-4-carboxylate-2-oxide Ethyl (4S,5S)-5-[(S)-1-cyclopropylcarbamoyl-3-methylbutylcarbamoyl]-1,3,2-dioxathiolane-4-carboxylate-2,2-dioxide Ethyl (4S,5S)-5-[(S)-1-cyclopentylcarbamoyl-3-methylbutylcarbamoyl]-1,3,2-dioxathiolane-4-carboxylate-2-oxide Ethyl (4S,5S)-5-[(S)-1-cyclopentylcarbamoyl-3-methylbutylcarbamoyl]-1,3,2-dioxathiolane-4-carboxylate-2,2-dioxide Ethyl (4S,5S)-5-[(S)-1-(4-guanidobutylcarbamoyl)-3-methylbutylcarbamoyl]-1,3,2-dioxathiolane-4-carboxylate-2,2-dioxide Ethyl (4S,5S)-5-[(S)-3-methyl-1-(N,N-dimethylcarbamoyl)butylcarbamoyl]-1,3,2-dioxathiolane-4-carboxylate-2,2-dioxide Ethyl (4S,5S)-5-[(S)-1-(N,N-diisopropylcarbamoyl)-3-methylbutylcarbamoyl]-1,3,2-dioxathiolane-4-carboxylate-2-oxide Ethyl (4S,5S)-5-[(S)-1-(N,N-diisopropylcarbamoyl)-3-methylbutylcarbamoyl]-1,3,2-dioxathiolane-4-carboxylate-2,2-dioxide Ethyl (4S,5S)-5-[(S)-3-methyl-1-(pyrrolidine-1-yl-carbonyl)butylcarbamoyl]-1,3,2-dioxathiolane-4-carboxylate-2,2-dioxide Ethyl (4S,5S)-5-[(S)-2-methyl-1-(3-methylbutylcarbamoyl)butylcarbamoyl]-1,3,2-dioxathiolane-4-carboxylate-2-oxide Ethyl (4S,5S)-5-[(S)-2-methyl-1-(3-methylbutylcarbamoyl)butylcarbamoyl]-1,3,2-dioxathiolane-4-carboxylate-2,2-dioxide Ethyl (4S,5S)-5-[(S)-1-(3-methylbutylcarbamoyl)methylthiopropylcarbamoyl]-1,3,2-dioxathiolane-4-carboxylate-2,2-dioxide (4S,5S)-5-[(S)-3-methyl-1-(3-methylbutylcarbamoyl)butylcarbamoyl]-1,3,2-dioxathiolane-4-carboxy-2-oxide Potassium (4S,5S)-5-[(S)-3-methyl-1-(3-methylbutylcarbamoyl)butylcarbamoyl]-1,3,2-dioxathiolane-4-carboxylate-2,2-dioxide Butyl (4S,5S)-5-[(S)-3-methyl-1-(3-methylbutylcarbamoyl)butylcarbamoyl]-1,3,2-dioxathiolane-4-carboxylate-2,2-dioxide Abbreviations used in the description of the examples to be presented below represent the following:

NMR nuclear magnetic resonance spectrum ($^1$H-NMR)
IR infrared absorption spectrum
SIMS secondary ion mass analysis spectrum
Boc tert-butoxycarbonyl group
Bu$^t$ tert-butyl group
Et ethyl group
mp melting point

REFERENCE EXAMPLE 1

Boc-L-leucylisoamylamide

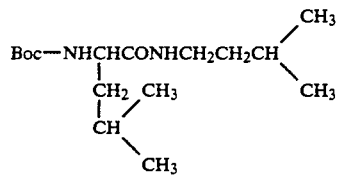

Boc-L-leucine-succinimide ester (7.00 g) and isoamylamine (1.86 g) were mixed in 1,2-dimethoxyethane (70 ml) under ice cooling, and the resultant mixture was stirred at room temperature for three hours. A proper amount of a 2.5% aqueous sodium carbonate solution was added to the reaction solution, and extraction was performed three times using ethyl acetate. The organic layer was washed with saturated sodium chloride solution and dried with magnesium sulfate, and the solvent was distilled off under a reduced pressure. As a result, 6.40 g of a target compound were obtained. NMR data of the product were as follows.

$^1$H-NMR (CDCl$_3$) δ ppm: 0.89–0.95 (12 H, m, —CH$_3$×4), 1.35–1.55 (9 H, m), 1.55–1.80 (6 H, m), 3.27 (2 H, q, J=6.9 Hz, —CONHCH$_2$—), 4.03 (1 H, m, >CHCONH—), 4.89 (1 H, br s, —NH-Boc), 6.12 (1 H, br s, —CONHCH$_2$—)

REFERENCE EXAMPLE 2

L-leucylisoamylamide·hydrobromide

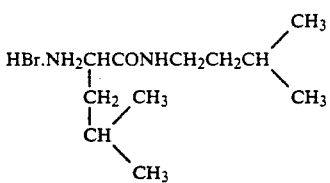

Boc-L-leucylisoamylamide (6.20 g) obtained in Reference Example 1 was dissolved in acetic acid (20 ml) and a 25% hydrobromic acid/acetic acid solution (50 ml) was added to the resultant solution under ice cooling. Thereafter, the solution mixture was stirred at room temperature for 30 minutes, and the reaction solution was subjected to distillation under reduced pressure. The obtained yellow viscous oily substance was washed with petroleum ether and ether. As a result, 5.86 g of a target compound were obtained as a yellowish white powder. NMR data of the compound was as follows.

$^1$H-NMR (CDCl$_3$) δ ppm: 0.89–1.10 (12H, m, —CH$_3$×4), 1.46 (2 H, q, J=6.9 Hz, —NHCH$_2$CH$_2$—), 1.60–2.00 (4H, m), 3.17 (1 H, br s, —NHCH$_2$—), 3.40 (1 H, br s, —NHCH$_2$—), 4.22 (1 H, br s, >CHCONH—), 4.39 (1 H, br s, -CONHCH$_2$—), 8.01 (2 H, br s, —NH$_2$).

REFERENCE EXAMPLE 3

L-leucyldibutylamide

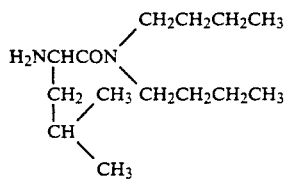

Following the same procedures as in Reference Examples 1 and 2, L-leucyldibutylamide·hydrobromide obtained from Boc-L-leucine-succinimide ester (1.50 g) and dibutylamine (553 mg) was treated with a saturated sodium bicarbonate aqueous solution to obtain 871 mg of a target compound. NMR data of the compound were as follows.

$^1$H—NMR (CDCl$_3$) δ ppm: 0.88–1.06 (12 H, m, —CH$_3$×4), 1.28–1.93 (11 H, m), 3.12 (2 H, m, >N—CH$_2$—), 3.29 (1 H, m, >N—CH$_2$—), 3.57 (2 H, m, >N—CH$_2$—, >CHCON<).

REFERENCE EXAMPLE 4

L-leucylbenzylamide

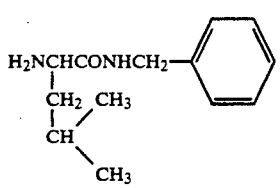

Following the same procedures as in Reference Examples 1, 2, and 3, 917 mg of a target compound were obtained from Boc-L-leucine-succinimide ester (1.52 g) and benzylamine (497 mg). NMR data of the compound were as follows.

$^1$H—NMR (CDCl$_3$) δ ppm: 0.84–1.08 (6 H, m, —CH$_3$×2), 1.30–1.83 (3 H, m), 3.43 (1 H, dd, J=2.9, 9.7 Hz, >CHCONH—), 4.44 (2 H, d, J=5.9 Hz, Ph—CH$_2$—), 7.30 (5 H, m, arom).

REFERENCE EXAMPLE 5

L-leucylpiperidylamide

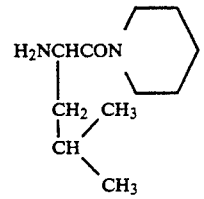

Following the same procedures as in Reference Examples 1, 2, and 3, 386 mg of a target compound were obtained from Boc-L-leucine-succinimide ester (1.61 g) and piperidine (420 mg). NMR data of the compound were as follows.

$^1$H—NMR (CDCl$_3$) δ ppm: 0.86–1.02 (6 H, m, —CH$_3$×2), 1.22–1.92 (9 H, m), 3.40 (2 H, m), 3.57 (2 H, m), 3.79 (1 H, m, >CHCON<).

REFERENCE EXAMPLE 6

L-leucyldecylamide

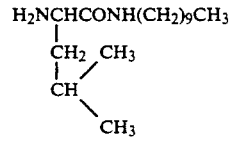

Following the same procedures as in Reference Examples 1, 2, and 3, 1.17 g of a target compound were obtained from Boc-L-leucine-succinimide ester (1.53 g) and decylamine (731 mg). NMR data of the compound were as follows. $^1$H—NMR (CDCl$_3$) δ ppm: 0.81–1.05 (9 H, m, —CH$_3$×3), 1.18–1.82 (19 H, m), 3.22 (2 H, q, J=7.0 Hz, —CONHCH$_2$—), 3.37 (1 H, dd, J=3.6, 9.8 Hz, >CHCONH—).

REFERENCE EXAMPLE 7

L-leu cylcyclohexylamide

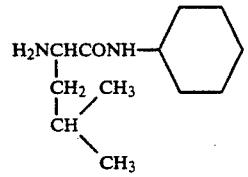

Following the same procedures as in Reference Examples 1, 2, and 3, 430 mg of a target compound were obtained from Boc-L-leucine-succinimide ester (1.06 g) and cyclohexylamine (320 mg). NMR data of the compound were as follows.

$^1$H—NMR (CDCl$_3$) δ ppm: 0.89–1.03 (6 H, m, —CH$_3$×2), 1.08–1.95 (13 H, m), 3.34 (1 H, m, —CONHCH<), 3.74 (1 H, m, >CHCONH<), 7.11 (1 H, br, s).

REFERENCE EXAMPLE 8

L-phenylalanylisoamylamide

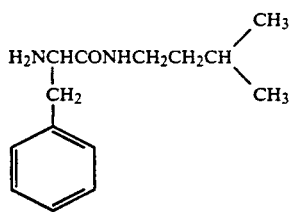

Following the same procedures as in Reference Examples 1, 2, and 3, 709 mg of a target compound were obtained from Boc-1-phenylalanine-succinimide ester (2.52 g) and isoamylamine (666 mg). NMR data of the compound were as follows.

$^1$H—NMR (CDCl$_3$) δ ppm: 0.82–1.01 (6 H, m, —CH$_3$×2), 1.31–1.45 (2 H, m), 1.51–1.67 (2 H, m), 2.69 (1 H, dd, J=9.3, 13.7 Hz), 3.21–3.36 (3 H, m), 3.59 (1 H, dd, J=4.1, 9.3 Hz), 7.16–7.39 (6 H, m, arom, —CONH—).

REFERENCE EXAMPLE 9

L-norleucylisoamylamide

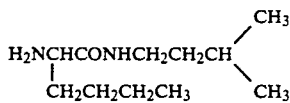

Following the same procedures as in Reference Examples 1, 2, and 3, 874 mg of a target compound were obtained from Boc-L-norleucine-succinimide ester (2.62 g) and isoamylamine (763 mg). NMR data of the compound were as follows.

$^1$H—NMR (CDCl$_3$) δ ppm: 0.76–1.03 (9 H, m, —CH$_3$×3), 1.20–1.92 (9 H, m), 3.18–3.39 (3 H, m), 7.22 (1 H, br s)

REFERENCE EXAMPLE 10

Monbenzyl D-tartrate ester

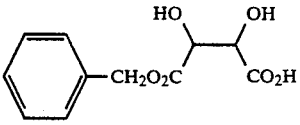

A target compound was synthesized in accordance with a method by M. J. Miller et al. [*J. Org. Chem.*, 47, 4928 (1982)].

Dicyclohexylcarbodiimide (4.94 g) was added under ice cooling to a solution prepared by dissolving D-tartaric acid (3.00 g) in anhydrous tetrahydrofuran (40 ml), and the resultant solution was stirred under ice cooling. Thereafter, the solution was stirred for five hours while the temperature was gradually raised to room temperature, and the produced dicyclohexyl urea was removed. Benzyl alcohol (4.12 ml) was added to the reaction filtrate, and the resultant solution was stirred at room temperature overnight. The reaction solution was condensed under reduced pressure, ethyl acetate (50 ml) was added to dissolve the reaction product, and extraction was performed using a 10% sodium carbonate solution. The extracted aqueous solution was adjusted to about pH 2, and then was extracted again with ethyl acetate. The extracted organic layer was washed with saturated sodium chloride solution and dried with magnesium sulfate, and the solvent was distilled off under reduced pressure to obtain a crude product. This crude product was recrystallized from chloroform to obtain 402 mg of a target compound. NMR data of the compound were as follows.

$^1$H—NMR (CDCl$_3$) δ ppm: 4.64 (2 H, d), 5.26 (2 H, br s, —CH$_2$Ph), 7.34 (5 H, br s, arom).

REFERENCE EXAMPLE 11

(1S,2S)-2-benzyloxycarbonyl-1,2-dihydroxyethanecarbonyl-L-leucine

Benzyl (2S,3S)-2,3-dihydroxy-3-[(S)-3-methyl-1-tert-butoxycarbonylbutylcarbamoyl]propionate was prepared from monobenzyl D-tartrate ester obtained in Reference Example 10 and leucine tert-butylester·hydrochloride by using dicyclohexylcarbodiimide and N-hydroxysuccinimide. This product (2.21 g) was dissolved in 20 ml of 4-N hydrochloric acid/dioxane, and the resultant solution was stirred under ice cooling while the temperature was gradually returned to room temperature, thereby obtaining 1.31 g of a target compound. NMR data of the compound were as follows.

$^1$H—NMR (CDCl$_3$) δ ppm: 0.89–1.09 (6 H, m, —CH$_3$×2), 1.62–1.90 (3 H, m, —CH$_2$CH(CH$_3$)$_2$), 4.48 (1 H, d, J=2.0 Hz), 4.54 (1 H, m, >CHCONH—), 4.59 (1 H, d, J=2.0 Hz), 5.19 (1 H, d, J=13.6 Hz, —CH$_2$Ph), 5.29 (1 H, d, J=13.6 Hz, —CH$_2$Ph), 7.30–7.50 (5H, m, arom).

EXAMPLE 1

Ethyl (4S,5S)-5-[(S)-3-methyl-1-(3-methylbutylcarbamoyl)butylcarbamoyl]-2-phenyl-1,3-dioxolane-4-carboxylate

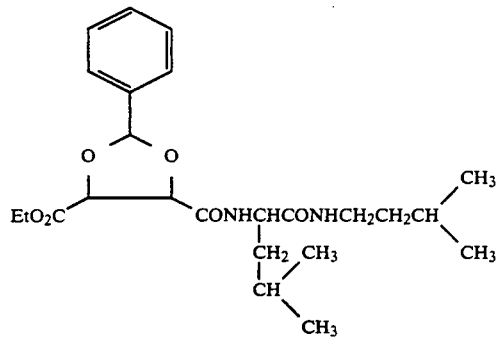

L-leucylisoamylamide·hydrobromide (1.90 g) obtained in Reference Example 2 was dissolved in dimethylformamide (40 ml). Triethylamine (1.35 ml) and diethyl cyanophosphonate (1.63 g) were sequentially added to the resultant solution under ice cooling, and the solution was stirred under ice cooling. A dimethylformamide (20 ml) solution of 2,3-O-benzylidene-ethyltartrate monoester [A. Tanaka et al. *Agric. Biol. Chem.*, 48, 2135 (1984)] (2.20 g) was added to the resultant solution under ice cooling, and the solution was stirred under ice cooling and then stirred at 4° C. overnight. The reaction solution was condensed to about 30 ml under reduced pressure, and 150 ml of an ethyl acetate/benzene solution mixture were added to the condensed solution. The organic layer was sequentially washed with 10% citric acid, water, saturated sodium bicarbonate solution, water, and saturated sodium chloride solution and dried with magnesium sulfate. The solvent was distilled off from the dried organic layer under reduced pressure to obtain a crude product. This crude product was purified by silica gel column chromatography (developing solvent; hexane:ethyl acetate=2:1) to obtain 2.22 g of a target compound in the form of white crystals. NMR data and SIMS data of the compound were as follows.

$^1$H—NMR (CDCl$_3$) δ ppm: 0.84–1.00 (12 H, m, —CH$_3$×4), 1.30–1.48 (5 H, m), 1.48–1.75 (4 H, m), 3.24 (2 H, m, —NHCH$_2$—), 4.20–4.50 (3 H, m), 4.78 (½ H, d, J=3.1 Hz), 4.91 (½ H, d, J=3.5 Hz), 4.93 (½ H, d, J=3.5 Hz), 5.02 (½ H, d, J=3.1 Hz), 6.00 (½ H, s, Ph—CH<), 6.02 (1 H, br s, —CONHCH$_2$—), 6.21 (½ H, s, Ph—CH<), 6.78 (½ H, d, J=8.9 Hz, —NHCHCO—), 7.04 (½ H, d, J=8.9 Hz, —NHCHCO—), 7.40–7.56 (5 H, m, arom.).

SIMS m/z; 449 (M+1).

EXAMPLE 2

Ethyl (2S,3S)-2,3-dihydroxy-3-[(S)-3-methyl-1-(3-methylbutylcarbamoyl)butylcarbamoyl]propionate

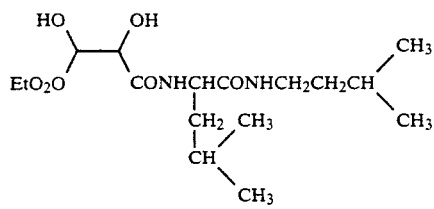

Ethyl (4S,5S)-5-[(S)-3-methyl-1-(3-methylbutylcarbamoyl)butylcarbamoyl]-2-phenyl-1,3-dioxolane-4-carboxylate (2.07 g) obtained in Example 1 was dissolved in acetic acid (40 ml). Palladium black (0.40 g) was added to the resultant solution, and the solution was strongly stirred at room temperature for 60 hours under a hydrogen flow at 4.1 atm. After the catalyst was filtered off, the filtrate was condensed under reduced pressure to obtain a crude product. The crude product was purified by silica gel column chromatography (a developing solvent; hexane:ethyl acetate=1:1→1:3) to obtain 1.38 g of a target compound. NMR data of the compound was as follows.

$^1$H—NMR (CDCl$_3$) δ ppm: 0.89–0.95 (12 H, m, —CH$_3$×4), 1.30 (3 H, t, J=7.1 Hz, —OCH$_2$CH$_3$), 1.33–1.45 (2 H, m), 1.50–1.72 (4 H, m), 3.24 (2 H, m, —NHCH$_3$), 3.52 (1 H, br s), 4.28 (2 H, q, J=7.1 Hz, —COCH$_2$CH$_3$), 4.45 (1 H, m, >CHCONH—), 4.49 (1 H, br s), 4.66 (1 H, br s), 4.91 (1 H, br s), 6.57 (1 H, t, J=4.4 Hz, —CONHCH$_2$—), 7.33 (1 H, d, J=8.6 Hz, —NHCHCO—).

EXAMPLE 3

Ethyl (4S,5S)-5-[(S)-3-methyl-1-(3-methylbutylcarbamoyl)butylcarbamoyl]-1,3,2-dioxathiolane-4-carboxylate-2-oxide

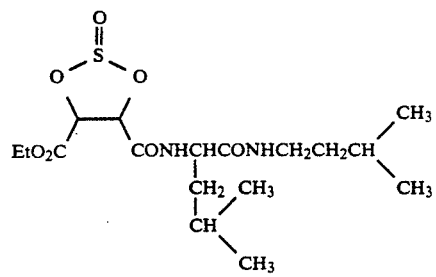

Ethyl (2S,3S)-2,3-dihydroxy-3-[(S)-3-methyl-1-(3-methylbutylcarbamoyl)butylcarbamoyl]propionate (305 mg) obtained in Example 2 was dissolved in carbon tetrachloride (6 ml). Thionyl chloride (69 μl) was added to the resultant solution at room temperature, and the solution was heated under reflux for 40 minutes. The reaction solution was condensed under reduced pressure to obtain a crude product. This crude product was purified by silica gel column chromatography (a developing solvent; hexane:ethyl acetate=2:1) to obtain 174 mg of a target compound as white crystals. This product was a diastereomer mixture due to 2-position asymmetry. Therefore, the mixture was subjected to silica gel column chromatography again to obtain a high-polarity isomer (compound A) and a low-polarity isomer (compound B). NMR data and SIMS data of the compounds A and B were as follows.

Compound A $^1$H—NMR (CDCl$_3$) δ ppm: 0.89–0.95 (12 H, m, —CH$_3$×4), 1.34 (3 H, t, J=7.1 Hz, —OCH$_2$CH$_3$), 1 36–1.50 (2 H, m), 1.50–1.70 (4 H, m), 3.26 (2 H, m, —NHCH$_2$—), 4.33 (2 H, q, J=7.1 Hz, —OCH$_2$CH$_3$), 4.35–4.40 (1 H, m, >CHCONH), 5.22 (1 H, d, J=3.7 Hz), 5.66 (1 H, d, J=3.7 Hz), 5.93 (1 H, br s, —CONHCH$_2$—), 6.94 (1 H, d, J=8.0 Hz, —NHCHCO—).

SIMS m/z; 407 (M+1).

Compound B $^1$H—NMR (CDCl$_3$) δ ppm: 0.89–0.95 (12 H, m, —CH$_3$×4), 1.34 (3 H, t, J=7.1 Hz, —OCH$_2$CH$_3$), 1.36–1.50 (2 H, m), 1.50–1.70 (4 H, m), 3.27 (2 H, m, —NHCH$_2$—), 4.33 (2 H, q, J=7.1 Hz, —OCH$_2$CH$_3$), 4.35–4.40 (1 H, m, >CHCONH), 5.38 (1 H, d, J=4.0 Hz), 5.72 (1 H, d, J=4.0 Hz), 5.90 (1 H, br s, —CONHCH$_2$—), 6.97 (1 H, d, J=8.0 Hz, —NHCHCO—).

SIMS m/z; 407 (M+1).

EXAMPLE 4

Ethyl (4S,5S)-5-[(S)-3-methyl-1-(3-methylbutylcarbamoyl)-butylcarbamoyl]-1,3,2-dioxathiolane-4-carboxylate-2,2-dioxide

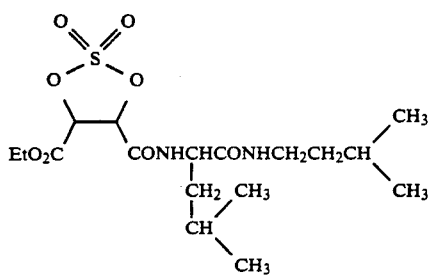

Following the same procedures as in Example 3, ethyl (2S,3S)-2,3-dihydroxy-3-[(S)-3-methyl-1-(3-methylbutylcarbamoyl)butylcarbamoyl]propionate (200 mg) was converted into ethyl-(4S,5S)-5-[(S)-3-methyl-1-(3-methylbutylcarbamoyl) butylcarbamoyl]-1,3,2-dioxathiolane-4-carboxylate-2-oxide. Acetonitrile (3 ml) was added to the reaction solution (carbon tetrachloride; 3 ml) without isolating or purifying the product, and the resultant solution was stirred at room temperature. Subsequently, a solution prepared by dissolving sodium periodate (252 mg) and ruthenium trichloride hydrate (catalytic amount) in water (4.5 ml) was added, and the resultant solution was stirred at room temperature for 20 hours. Diethylether was added to the reaction solution, and the ether layer of the solution was sequentially washed with water, saturated sodium bicarbonate solution, and saturated sodium chloride solution. The resultant layer was dried with magnesium sulfate, and the solvent was distilled off under reduced pressure to obtain a crude product. This crude product was purified by silica gel column chromatography (a developing solvent; hexane:ethyl acetate=2:1) to obtain 117 mg of a target compound as a white powder. NMR data, IR data, and SIMS data of the compound were as follows.

$^1$H—NMR (CDCl$_3$) δ ppm: 0.89–0.96 (12 H, m, —CH$_3$×4), 1.36 (3 H, t, J=7.2 Hz, —OCH$_2$CH$_3$), 1.35–1.50 (2 H, m), 1.50–1.73 (4 H, m), 3.30 (2 H, m, —NHCH$_2$—), 4.37 (2 H, q, J=7.2 Hz, —OCH$_2$CH$_3$), 4.50 (1 H, m, >CHCONH—), 5.51 (1 H, d, J=4.0 Hz), 5.53 (1 H, d, J=4.0 Hz), 6.28 (1 H, t, J=4.9 Hz, —CONHCH$_2$—), 7.47 (1 H, d, J=8.0 Hz, —NHCHCO—).

IR $\nu_{max}^{CHCl_3}$ cm$^{-1}$: 1750, 1677, 1413, 1229.

SIMS m/z; 423 (M+1).

EXAMPLE 5

Ethyl (4R,5R)-5-[(S)-3-methyl-1-(3-methylbutylcarbamoyl)-butylcarbamoyl]-2-phenyl-1,3-dioxolane-4-carboxylate

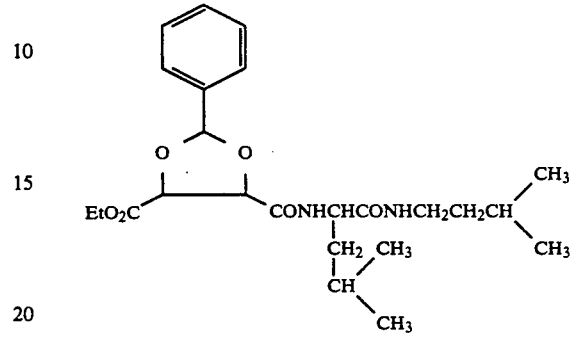

Following the same procedures as in Example 1, 3.38 g of a target compound were obtained from L-leucylisoamylamide hydrobromide (2.50 g) obtained in Reference Example 2 and 2,3-O-benzylidene-L-monoethylester tartarate (3.00 g). NMR data of the compound were as follows.

$^1$H-NMR (CDCl$_3$) δ ppm: 0.88–0.97 (12 H, m, —CH$_3$×4), 1.30–1.50 (5 H, m) 1.50–1.70 (4 H, m), 3.27 (2 H, m, —NHCH$_2$—), 4.30–4.50 (3H, m, —OCH$_2$CH$_3$, >CHCONH—), 4.79 (½ H, d, J=3.5 Hz), 4.88 (½ H, d, J=4.4 Hz), 4.92 (½ H, d, J=4.4 Hz), 4.94 (½ H, d, J=3.5 Hz), 5.97 (1 H, br s, —CONHCH$_2$—), 6.00 (½ H, s, Ph—CH<), 6.17 (½ H, s, Ph—CH<), 6.85 (½ H, d, J=8.6 Hz, —NHCHCO—), 7.12 (½ H, d, J=8.6 Hz, —NHCHCO—), 7.40–7.60 (5 H, m, arom.)

EXAMPLE 6

Ethyl (2R,3R)-2,3-dihydroxy-3-[(S)-3-methyl-1-(3-methylbutylcarbamoyl)butylcarbamoyl]propionate

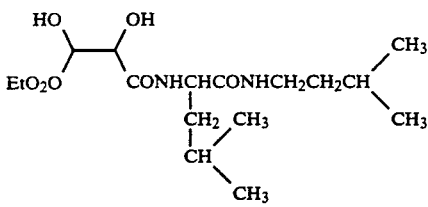

Following the same procedures as in Example 2, 654 mg of a target compound were prepared from ethyl (4R,5R)-5-[(S)-3-methyl-1-(3-methylbutylcarbamoyl)-butylcarbamoyl]-2-phenyl-1,3-dioxolane-4-carboxylate (1.00 g) obtained in Example 5. NMR data of the compound were as follows.

$^1$H-NMR (CDCl$_3$) δ ppm: 0.86–0.96 (12 H, m, —CH$_3$×4), 1.31–1.45 (5 H, m), 1.50–1.75 (4 H, m), 3.20 (2 H, m, —NHCH$_2$—), 4.27 (2 H, m, —OCH$_2$CH$_3$), 4.47 (1 H, m, >CHCONH—), 4.55 (1 H, br s), 4.68 (1 H, br s), 5.35 (1 H, br s), 6.99 (1 H, t, J=4.9 Hz, —CONHCH$_2$—), 7.61 (1 H, d, J=8.5 Hz, —NHCHCO—).

EXAMPLE 7

Ethyl (4R,5R)-5-[(S)-3-methyl-1-(3-methylbutylcarbamoyl)-butylcarbamoyl]-1,3,2-dioxathiolane-4-carboxylate-2-oxide

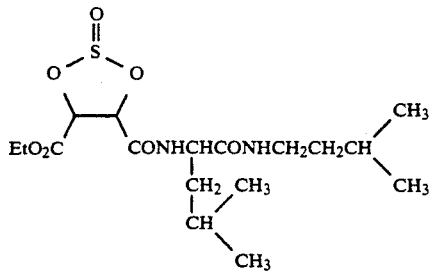

Following the same procedures as in Example 3, 28 mg of a target compound were prepared from ethyl (2R,3R)-2,3-dihydroxy-3-[(S)-3-methyl-1-(3-methylbutylcarbamoyl)butylcarbamoyl]propionate (150 mg) obtained in Example 6. This compound was a diastereomer mixture due to 2-position asymmetry. Therefore, the compound was subjected to silica gel column chromatography to obtain a high-polarity isomer (compound C) and a low-polarity isomer (compound D). NMR data of the compounds C and D were as follows.

High-polarity isomer (C)

$^1$H—NMR (CDCl$_3$) δ ppm: 0.86–0.97 (12 H, m, —CH$_3$×4), 1.30–1.50 (5 H, m), 1.50–1.93 (4 H, m), 3.20 (2 H, m, —NHCH$_2$—), 4.33 (2 H, q, J=7.1 Hz, —OCH$_2$CH$_3$), 4.40–4.55 (1 H, m, >CHCONH—), 5.36 (1 H, d, J=2.7 Hz), 5.84 (1 H, d, J=2.7 Hz), 6.45 (1 H, br s, —CONHCH$_2$—), 6.66 (1 H, d, J=8.8 Hz).

Low-polarity isomer (D)

$^1$H—NMR (CDCl$_3$) δ ppm 0.89–0.95 (12 H, m, —CH$_3$×4), 1.30–1.50 (5 H, m), 1.50–1.93 (4 H, m), 3.22 (2 H, m, —NHCH$_2$—), 4.32 (2 H, q, J=7.1 Hz, —OCH$_2$CH$_3$), 4.38–4.45 (1 H, m, >CHCONH—), 5.33 (1 H, d, J=4.4 Hz), 5.72 (1 H, d, J=4.4 Hz), 6.10 (1 H, br s, —CONHCH$_2$—), 7.18 (1 H, d, J=8.5 Hz).

EXAMPLE 8

Ethyl (4R,5R)-5-[(S)-3-methyl-1-(3-methylbutylcarbamoyl)-butylcarbamoyl]-1,3,2-dioxathiolane-4-carboxylate-2,2-dioxide

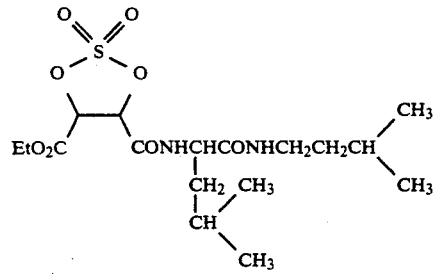

Following the same procedures as in Example 3, ethyl (4R,5R)-5-[(S)-3-methyl-1-(3-methylbutylcarbamoyl)butylcarbamoyl]-1,3,2-dioxathiolane-4-carboxylate-2-oxide was prepared from ethyl (2R,3R)-2,3-dihydroxy-3-[(S)-3-methyl-1-(3-methylbutylcar- bamoyl)butylcarbamoyl]propionate (40 mg). Subsequently, 30 mg of a target compound were obtained following the same procedures as in Example 4. NMR data of the compound were as follows.

$^1$H—NMR (CDCl$_3$) δ ppm: 0.89–0.97 (12 H, m, —CH$_3$×4), 1.30–1.50 (5 H, m), 1.50–1.90 (4 H, m), 3.25 (2 H, m, —NHCH$_2$—), 4.38 (2 H, q, J=7.2 Hz, —OCH$_2$CH$_3$), 4.50 (1 H, m, >CHCONH—), 5.51 (1 H, d, J=4.1 Hz), 5.53 (1 H, d, J=4.1 Hz), 6.10 (1 H, br s, —CONHCH$_2$—), 7.18 (1 H, d, J=8.5 Hz, —NHCHCO—).

EXAMPLE 9

(2S,3S)-2,3-dihydroxy-3-[(S)-3-methyl-1-(3-methylbutylcarbamoyl)butylcarbamoyl]propionic acid

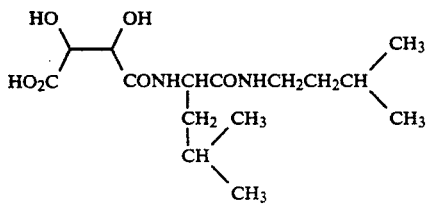

Ethyl (2S,3S)-2,3-dihydroxy-3-[(S)-3-methyl-1-(3-methylbutylcarbamoyl)butylcarbamoyl]propionate (309 mg) obtained in Example 2 was dissolved in methanol. 2N KOH (472 μl) was added to the resultant solution, and the solution was stirred at 0° C. for two hours. Thereafter, the solvent was distilled off under reduced pressure, sodium bicarbonate solution was added to adjust the pH to be about 8, and the aqueous layer was washed with ethyl acetate. Subsequently, the pH was adjusted to about 2 with dilute hydrochloric acid, sodium chloride was added until the solution was saturated, and the aqueous layer was extracted with ethyl acetate. The extracted organic layer was washed with sodium chloride solution and dried with magnesium sulfate, and the solvent was distilled off under reduced pressure, thereby obtaining 264 mg of a target compound. NMR data of the compound were as follows.

$^1$H—NMR (CDCl$_3$) δ ppm: 0.80–1.06 (12 H, m, —CH$_3$×4), 1.30–1 47 (2 H, m), 1.53–1.75 (4 H, m), 3.11 (1 H, m, —NHCH$_2$—), 3.31 (1 H, m, —NHCH$_2$—), 4.50 (1 H, m, >CHCONH—), 4.56 (1 H, br s), 4.62 (1 H, br s), 7.25 (1 H, br s), 7.88 (1 H, br s).

EXAMPLE 10

Benzyl (2S,3S)-2,3-dihydroxy-3-[(S)-3-methyl-1-(3-methylbutylcarbamoyl)butylcarbamoyl]propionate

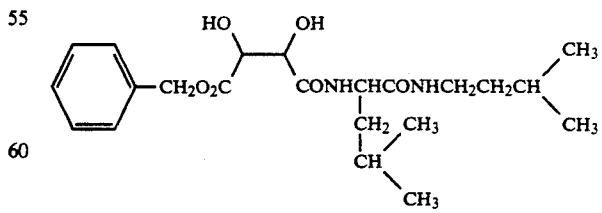

(2S,3S)-2,3-dihydroxy-3-[(S)-3-methyl-1-(3-methylbutylcarbamoyl)butylcarbamoyl]propionic acid (1.40 g) obtained in Example 9 and sodium bicarbonate (712 mg) were suspended in dimethylformamide (20 ml). A dimethylformamide (20 ml) solution of benzyl bromide (3.56 g) was added to the resultant suspension, and the suspension was stirred at room temperature for 24 hours. Water was added after the reaction, and then was extracted with ethyl acetate. The organic layer was sequentially washed with water and saturated sodium chloride solution. After the resultant layer was dried with magnesium sulfate, the solvent was distilled off under reduced pressure to obtain a crude product. This crude product was purified by silica gel column chromatography (a developing solvent; hexane:ethyl acetate=1:1→1:3) to obtain 1.13 g of a target compound. NMR data of the compound were as follows.

$^1$H—NMR (CDCl$_3$) δ ppm: 0.78–1.03 (12 H, m, —CH$_3$×4), 1.28–1.40 (2 H, m), 1.48–1.72 (4 H, m), 3.18 (2 H, m, —NHCH$_2$—), 3.61 (1 H, d, J=7.7 Hz, —OH) 4.47 (1 H, m, >CHCONH—) 4.52 (1 H, dd, J=7.2, 1.8 Hz), 4.71 (1 H, dd, J=7.7, 1.9 Hz), 5.12–5.31 (3 H, m, Ph—CH$_2$—, —OH), 6.70 (1 H, t, J=5.9 Hz, —CONHCH$_2$—), 7.34 (1 H, m, arom), 7.40 (1 H, d, J=8.7 Hz, —NHCHCO—)

EXAMPLE 11

Benzyl (4S,5S)-5-[(S)-3-methyl-1-(3-methylbutylcarbamoyl)-butylcarbamoyl]-1,3,2-dioxathiolane-4-carboxylate-2,2-dioxide

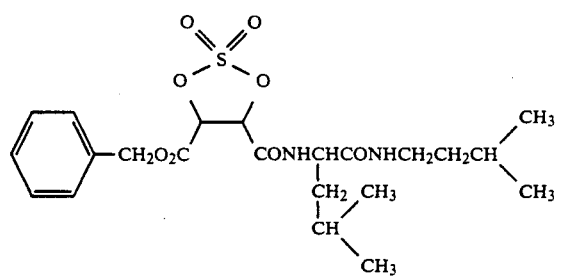

Following the same procedures as in Example 4, 981 mg of a target compound were prepared from benzyl (2S,3S)-2,3-dihydroxy-3-[(S)-3-methyl-1-(3-methylbutylcarbamoyl)butylcarbamoyl]propionate (1.70 g) obtained in Example 10. NMR data and SIMS data of the compound were as follows.

$^1$H—NMR (CDCl$_3$) δ ppm: 0.80–1.05 (12 H, m, —CH$_3$×4), 1.35–1.50 (2 H, m), 1.55–1.71 (4 H, m), 3.28 (2 H, m, —NHCH$_2$—), 4.47 (1 H, m, >CHCONH—), 5.31 (2 H, s, Ph—CH$_2$—), 5.47 (1 H, d, J=3.7 Hz), 5.54 (1 H, d, J=3.7 Hz), 5.91 (1 H, br s, —CONHCH$_2$—), 7.11 (1 H, d, J=8.2 Hz, —NHCHCO—), 7.37 (1 H, s, arom), SIMS m/z: 485 (M +1).

EXAMPLE 12

(4S,5S)-5-[(S)-3-methyl-1-(3-methylbutylcarbamoyl)-butylcarbamoyl]-1,3,2-dioxathiolane-4-carboxy-2,2-dioxide

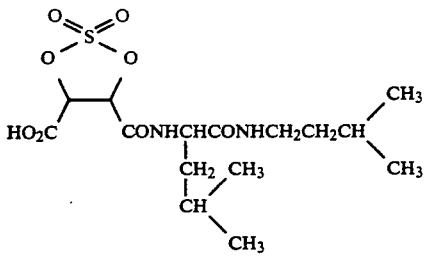

Benzyl (4S,5S)-5-[(S)-3-methyl-1-(3-methylbutylcarbamoyl)butylcarbamoyl]-1,3,2-dioxathiolane-4-carboxylate-2,2-dioxide (1.07 g) obtained in Example 11 was dissolved in tetrahydrofuran (65 ml), 10% palladium carbon (110 mg) was added to the resultant solution, and the solution was stirred at room temperature for four hours under a hydrogen flow. After the catalyst was filtered out, the resultant filtrate was condensed under reduced pressure to obtain 1.05 g of a target compound. NMR data, IR data, and SIMS data of the compound were as follows.

$^1$H—NMR (CDCl$_3$) δ ppm: 0.82–1.03 (12 H, m, —CH$_3$×4), 1.35–1.46 (2 H, m), 1.50–1.79 (4 H, m), 3.11–3.41 (2 H, m, —NHCH$_2$—), 4.49 (1 H, m, >CHCONH—), 5.51 (2 H, m), 6.63 (1 H, br s, —CONHCH$_2$—), 7.72 (1 H, d, J=8.3 Hz, —NHCHCO—).

IR $\nu_{max}^{CHCl_3}$ cm$^{-1}$: 1749, 1689, 1637, 1528, 1413, 1213.

SIMS m/z; 395 (M+1).

EXAMPLE 13

Ethyl (2S,3S)-2,3-dihydroxy-3-[(S)-1-(N,N-dibutylcarbamoyl)-3-methylbutylcarbamoyl]propionate

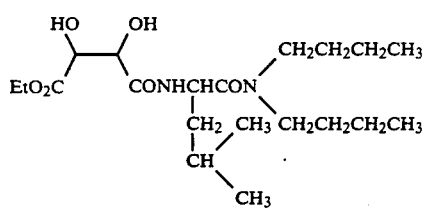

L-leucyldibutylamide obtained in Reference Example 3 was reacted following the same procedures as in Example 1. Subsequently, 1.05 g of a target compound were prepared from the obtained compound following the same procedures as in Example 2. NMR data of the target compound were as follows.

$^1$H—NMR (CDCl$_3$) δ ppm: 0.83–1.09 (12 H, m, —CH$_3$×4), 1.22–1.81 (14 H, m), 3.10 (1 H, m, >N—CH$_2$—), 3.30 (2 H, t, J=8.0 Hz, >N—CH$_2$—), 3.42–3.61 (2 H, m, >N—CH$_2$—, —OH), 4.31 (2 H, m, —OCH$_2$CH$_3$), 4.51 (1 H, dd, J=1.8, 7.2 Hz), 4.68 (1 H, dd, J=1.8, 7.4 Hz), 4.89 (1 H, d, J=7.2 Hz, —OH), 4.99 (1 H, m, >CHCON<), 7.44 (1 H, d, J=9.0 Hz, —NHCHCO—)

EXAMPLE 14

Ethyl (4S,5S)-5-(S)-1-(N,N-dibutylcarbamoyl)-3-methylbutylcarbamoyl]-1,3,2-dioxathiolane-4-carboxylate-2,2-dioxide

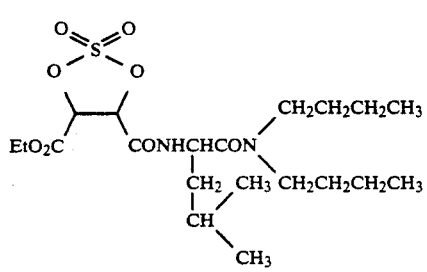

Following the same procedures as in Example 4, 53 mg of a target compound were prepared as a colorless transparent oily product from ethyl (2S,3S)-2,3-dihydroxy-3-[(S)-1-(N,N-dibutylcarbamoyl)-3-methylbutylcarbamoyl]propionate (188 mg) obtained in Example 13. NMR data and SIMS data of the target compound were as follows.

$^1$H—NMR (CDCl$_3$) δ ppm: 0.86–1.07 (12 H, m, —CH$_3$×4), 1.36 (3 H, t, J=7.1 Hz, —OCH$_2$CH$_3$), 1.25–1.72 (11 H, m), 3.07 (1 H, m, >N—CH$_2$—), 3.26 (2 H, m, >N—CH$_2$—), 3.56 (1 H, m, >N—CH$_2$—), 4.36 (2 H, q, J=7.1 Hz, —OCH$_2$CH$_3$), 4.96 (1 H, m, >CHCON<), 5.47 (1 H, d, J=4.0 Hz), 5.52 (1 H, d, J=4.0 Hz), 7.32 (1 H, d, J=8.8 Hz, —NHCHCO—).

SIMS m/z; 465 (M+1).

EXAMPLE 15

Ethyl (2S,3S)-2,3-dihydroxy-3-[(S)-1-benzylcarbamoyl-3-methylbutylcarbamoyl]propionate

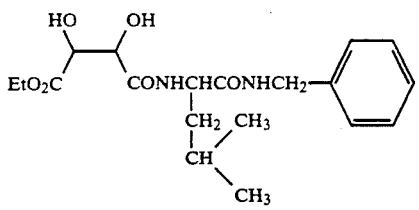

L-leucylbenzylamide obtained in Reference Example 4 was reacted following the same procedures as in Example 1, and the obtained compound was reacted following the same procedures as in Example 2, thereby obtaining 986 mg of a target compound. NMR data of the target compound were as follows.

$^1$H—NMR (CDCl$_3$) δ ppm: 0.78–1.00 (6 H, m, —CH$_3$×2), 1.23 (3 H, t, J=7.1 Hz, —OCH$_2$CH$_3$), 1.51–1.70 (3 H, m), 3.67 (1 H, d, J=7.2 Hz, —OH), 4.08–4.21 (3 H, m), 4.33–4.46 (2 H, m), 4.51–4.67 (2 H, m), 5.47 (1 H, d, J=6.4 Hz, —OH), 7.11–7.34 (5 H, m, arom), 7.53 (1 H, d, J=8.6 Hz, —NHCHCO—), 7.64 (1 H, t, J=5.6 Hz, —CONHCH$_2$—)

EXAMPLE 16

Ethyl (4S,5S)-5-[(S)-1-benzylcarbamoyl-3-methylbutylcarbamoyl]-1,3,2-dioxathiolane-4-carboxylate-2,2-dioxide

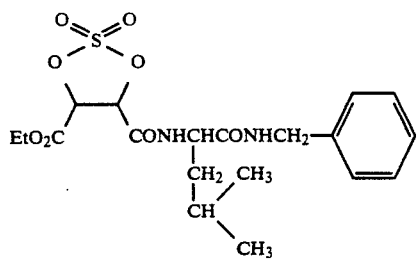

Following the same procedures as in Example 4, 363 mg of a target compound were prepared as white crystals from ethyl (2S,3S)-2,3-dihydroxy-3-[(S)-1-benzylcarbamoyl-3-methylbutylcarbamoyl]propionate (473 mg) obtained in Example 15. NMR data, IR data, SIMS data, and a melting point of the target compound were as follows.

$^1$H—NMR (CDCl$_3$) δ ppm: 0.93 (6 H, t, J=5.9 Hz, —CH$_3$×2), 1.36 (3 H, t, J=7.2 Hz, —OCH$_2$CH$_3$), 1.58–1.72 (3 H, m), 4.32–4.55 (5 H, m, —OCH$_2$CH$_3$, Ph—CH$_2$—, >CHCONH—), 5.45 (2 H, dd, J=3.8, 8.7 Hz), 6.29 (1 H, t, J=4.8 Hz, —CONHCH$_2$—), 7.04 (1 H, d, J=8.2 Hz, —NHCHCO—), 7.21–7.40 (5 H, m, arom)

IR ν$_{max}^{CHCl_3}$: cm$^{-1}$: 1750, 1678, 1522, 1413, 1216, SIMS m/z; 443 (M+1).
mp; 141.0°–142.0° C.

EXAMPLE 17

Ethyl (2S,3S)-2,3-dihydroxy-3-[(S)-3-methyl-1-(piperidine-1-ylcarbonyl)butylcarbamoyl]propionate

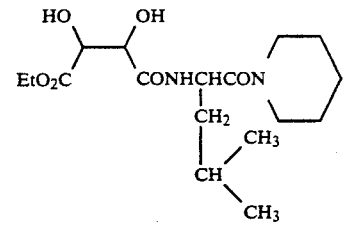

L-leucylpiperidylamide obtained in Reference Example 5 was reacted following the same procedures as in Example 1, and the obtained compound was reacted following the same procedures as in Example 2, thereby obtaining 512 mg of a target compound. NMR data of the target compound were as follows.

$^1$H—NMR (CDCl$_3$) δ ppm: 0.85–1.07 (6 H, m, —CH$_3$×2), 1.30 (3 H, t, J=7.2 Hz, —OCH$_2$CH$_3$), 1.34–1.78 (9 H, m), 3.40–3.61 (5 H, m), 4.28 (2 H, m, —OCH$_2$CH$_3$) 4.48 (1 H, dd, J=2.0, 7.5 Hz), 4.67 (1 H, dd, J=2.0, 7.6 Hz), 4.89 (1 H, d, J=7.5 Hz, —OH), 5.04 (1 H, m, >CHCON<), 7.49 (1 H, d, J=8.9 Hz, —NHCHCO—)

EXAMPLE 18

Ethyl (4S,5S)-5-[(S)-3-methyl-1-(piperidine-1-yl-carbonyl)-butylcarbamoyl]-1,3,2-dioxathiolane-4-carboxylate-2,2-dioxide

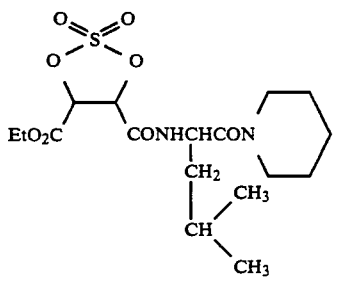

Following the same procedures as in Example 4, 90 mg of a target compound were prepared from ethyl (2S,3S)-2,3-dihydroxy-3-[(S)-3-methyl-1-(piperidine-1-yl-carbonyl)butylcarbamoyl]propionate obtained in Example 17. NMR data of the target compound were as follows.

$^1$H—NMR (CDCl$_3$) δ ppm: 0.92 (3 H, d, J=6.4 Hz, —CH$_3$), 0.99 (3 H, d, J=6.4 Hz, —CH$_3$), 1.36 (3 H, t, J=7.1 Hz, —OCH$_2$CH$_3$), 1.41–1.73 (9 H, m), 3.42 (2 H, br s), 3.58 (2 H, m), 4.38 (2 H, m, —OCH$_2$CH$_3$), 5.01 (1 H, m, >CHCON<), 5.45 (1 H, d, J=3.9 Hz), 5.52 (1 H, d, J=3.9 Hz), 7.28 (1 H, br s, —NHCHCO—)

EXAMPLE 19

Ethyl (2S,3S)-2,3-dihydroxy-3-[(S)-1-decylcarbamoyl-3-methylbutylcarbamoyl]propionate

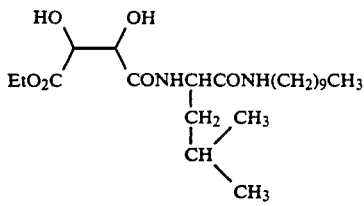

L-leucyldecylamide obtained in Reference Example 6 was reacted following the same procedures as in Example 1, and the obtained compound was reacted following the same procedures as in Example 2, thereby obtaining 1.05 g of a target compound. NMR data of the target compound were as follows.

$^1$H—NMR (CDCl$_3$) δ ppm: 0.79–1.01 (9 H, m, —CH$_3$×3), 1.14–1.73 (22 H, m), 3.20 (2 H, m, —NHCH$_2$—), 3.52 (1 H, d, J=7.1 Hz, —OH), 4.28 (2 H, m, —OCH$_2$CH$_3$), 4.46 (2 H, m), 4.65 (1 H, d, J=6.9 Hz), 4.84 (1 H, d, J=7.2 Hz), 6.54 (1 H, br s, —CONHCH$_2$—), 7.31 (1 H, d, J=8.5 Hz, —NHCHCO—)

EXAMPLE 20

Ethyl (4S,5S)-5-[(S)-1-decylcarbamoyl-3-methylbutylcarbamoyl]-1,3,2-dioxathiolane-4-carboxylate-2,2-dioxide

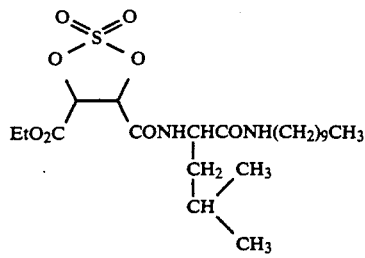

Following the same procedures as in Example 4, 286 mg of a target compound were obtained as white crystals from ethyl (2S,3S)-2,3-dihydroxy-3-[(S)-1-decylcarbamoyl-3-methylcarbamoyl]propionate (444 mg) obtained in Example 19. NMR data, SIMS data, and a melting point of the target compound were as follows.

$^1$H—NMR (CDCl$_3$) 0.81–1.00 (9 H, m, —CH$_3$×3), 1.18–1.70 (18 H, m), 1.37 (3 H, t, J=7.1 Hz, —OCH$_2$CH$_3$), 3.27 (2 H, m, —NHCH$_2$—), 4.30–4.46 (3H, m, —OCH$_2$CH$_3$, >CHCONH—), 5.48 (2 H, dd, J=3.8, 5.8 Hz), 5.80 (1 H, br s, —CONHCH$_2$—), 6.96 (1 H, d, J=8.1 Hz, —NHCHCO—)

SIMS m/z; 493 (M+1), mp; 114.0°–114.6° C.

EXAMPLE 21

Ethyl (2S,3S)-2,3-dihydroxy-3[(S)-1-cyclohexylcarbamoyl-3-methylbutylcarbamoyl]propionate

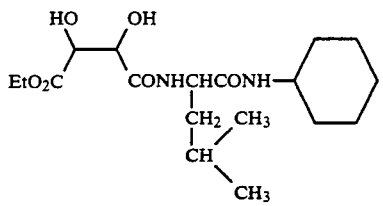

L-leucylcyclohexylamide obtained in Reference Example 7 was reacted following the same procedures as in Example 1, and the obtained compound was reacted following the same procedures as in Example 2, thereby obtaining 415 mg of a target compound. NMR data of the target compound were as follows.

$^1$H—NMR (CDCl$_3$) δ ppm: 0.80–1.02 (6 H, m, —CH$_3$×2), 1.09–1.38 (5 H, m), 1.31 (3 H, t, J=7.2 Hz, —OCH$_2$CH$_3$), 1.50–1.91 (8 H, m), 3.51 (1 H, d, J=7.3 Hz, —OH), 3.68 (1 H, m), 4.26 (2 H, m, —OCH$_2$CH$_3$), 4.40 (1 H, m, >CHCONH—), 4.49 (1 H, d, J=7.1 Hz), 4.66 (1 H, dd, J=1.7, 7.2 Hz), 4.99 (1 H, d, J=7.3 Hz, —OH), 6.41 (1 H, d, J=8.1 Hz), 7.34 (1 H, d, J=8.6 Hz)

EXAMPLE 22

Ethyl (4S,5S)-5-[(S)-1-cyclohexylcarbamoyl-3-methylbutylcarbamoyl]-1,3,2-dioxathiolane-4-carboxylate-2,2-dioxide

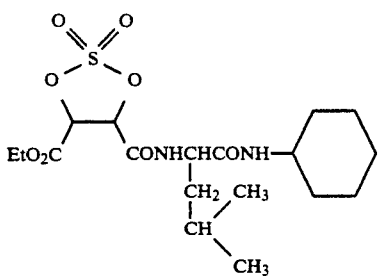

Following the same procedures as in Example 4, 151 mg of a target compound were prepared as white crystals from ethyl (2S,3S)-2,3-dihydroxy-3-[(S)-1-cyclohexylcarbamoyl-3-methylbutylcarbamoyl]propionate (415 mg) obtained in Example 21. NMR data and a melting point of the target compound were as follows.

$^1$H—NMR (CDCl$_3$) δ ppm: 0.81–1.01 (6 H, m, —CH$_3$×2), 1.08–1.47 (5 H, m), 1.36 (3 H, t, J=7.2 Hz, —OCH$_2$CH$_3$), 1.56–1.78 (6 H, m), 1.82–1.96 (2 H, m), 3.74 (1 H, m), 4.26–4.46 (3 H, m, —OCH$_2$CH$_3$, >CHCONH—), 5.50 (2 H, dd, J=3.9, 7.2 Hz), 5.74 (1 H, d, J=8.6 Hz), 7.10 (1 H, d, J=8.0 Hz)

mp: 176.7°–177.1° C.

EXAMPLE 23

Benzyl (2S,3S)-2,3-dihydroxy-3-[(S)-1-(3-methylbutylcarbamoyl)-2-phenylethylcarbamoyl]propionate

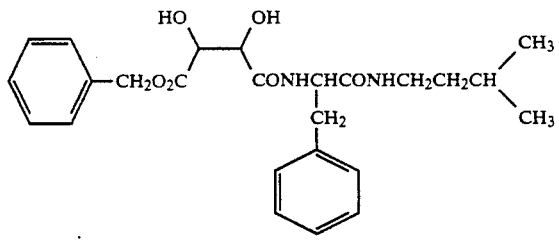

Monobenzyl D-tartarate ester (150 mg) obtained in Reference Example 10 was dissolved in dimethylformamide (6 ml). N-dihydroxysuccinimide (66 mg) and dicyclohexylcarbodiimide (142 mg) were sequentially added to the resultant solution under ice cooling, and the solution was stirred under ice cooling. Thereafter, the temperature was gradually returned to room temperature. After two hours, a dimethylformamide (2 ml) solution of L-phenylalanylisoamylamide (146 mg) obtained in Reference Example 8 was added to the resultant solution under ice cooling, and the solution was stirred under ice cooling. The solution was stirred overnight while the temperature was gradually returned to room temperature. The reaction solution was subjected to distillation under reduced pressure, and ethyl acetate was added. The organic layer was sequentially washed with saturated sodium bicarbonate solution and saturated sodium chloride solution and dried with magnesium sulfate, and the solvent was distilled off under reduced pressure, thereby obtaining a crude product. This crude product was purified by silica gel column chromatography (a developing solvent: chloroform:methanol=30:1) to obtain 220 mg of a target compound. NMR data of the compound were as follows.

$^1$H—NMR (CDCl$_3$) δ ppm: 0.69–0.90 (6 H, m, —CH$_3$×2), 1.06–1.19 (2 H, m), 1.22–1.39 (1 H, m), 2.88–3.18 (4 H, m), 3.52 (1 H, d, J=7.0 Hz), 4.43–4.67 (3 H, m), 4.71 (1 H, d, J=6.6 Hz), 5.20 (1 H, d, J=12.1 Hz, —CH$_2$Ph), 5.26 (1 H, d, J=12.1 Hz, —CH$_2$Ph), 5.85 (1 H, br s, —CONHCH$_2$—), 7.08–7.38 (10 H, m, arom), 7.48 (1 H, d, J=8.0 Hz, —NHCHCO—)

EXAMPLE 24

Benzyl (4S,5S)-5-[(S)-1-(3-methylbutylcarbamoyl)-2-phenylethylcarbamoyl]-1,3,2-dioxathiolane-4-carboxylate-2,2-dioxide

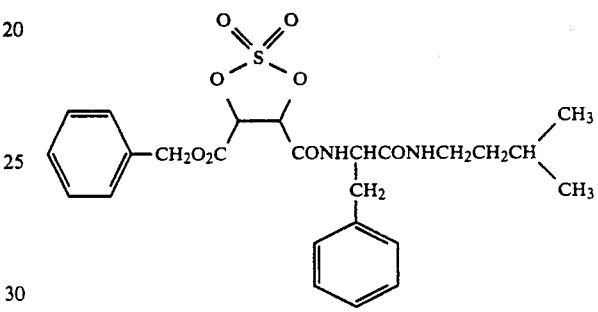

Following the same procedures as in Example 4, 106 mg of a target compound were prepared as white crystals from benzyl (2S,3S)-2,3-dihydroxy-3-[(S)-1-(3-methylbutylcarbamoyl)-2-phenylethylcarbamoyl]propionate (180 mg) obtained in Example 23. NMR data, SIMS data, and a melting point of the target compound were as follows.

$^1$H—NMR (CDCl$_3$) δ ppm: 0.80–0.91 (6 H, m, —CH$_3$×2), 1.16–1 27 (2 H, m), 1.35–1.48 (1 H, m), 2.97–3.28 (4 H, m), 4.56 (1 H, m, >CHCONH—), 5.31 (2 H, br s, —CH$_2$Ph), 5.32 (1 H, d, J=4.1 Hz), 5.43 (1 H, d, J=4.1 Hz), 7.17–7.43 (10 H, m, arom)

SIMS m/z; 519 (M+1).

mp; 147.5°–148.5° C.

EXAMPLE 25

Benzyl (2S,3S)-2,3-dihydroxy-3-[(S)-1-(3-methylbutylcarbamoyl)pentylcarbamoyl]propionate

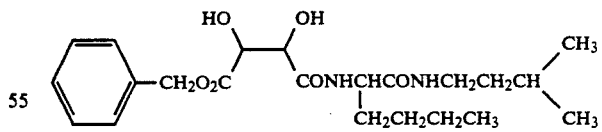

Following the same procedures as in Example 23, 235 mg of a target compound were prepared from monobenzyl D-tartrate ester (166 mg) obtained in Reference Example 10 and L-norleucylisoamylamide (152 mg) obtained in Reference Example 9. NMR data of the target compound were as follows.

$^1$H—NMR (CDCl$_3$) δ ppm: 0.79–0.94 (9 H, m, —CH$_3$×3), 1.18–1.40 (6 H, m), 1.46–1.82 (3 H, m), 3.20 (2 H, m, —NHCH$_2$—), 3.52 (1 H, d, J=7.2 Hz), 4.35 (1 H, q, J=7.2 Hz, >CHCONH—), 4.50 (1 H, dd, J=1.8, 7.2 Hz), 4.65 (1 H, d, J=7.2 Hz), 4.71 (1 H, dd, J=1.8, 7.2 Hz), 5.20 (1 H, d, J=12.2 Hz, —CH₂Ph), 5.26 (1 H, d, J=12.2 Hz, —CH₂Ph), 6.40 (1 H, t, J=5.6 Hz, —CONHCH₂—), 7.27-7.41 (6 H, m)

EXAMPLE 26

Benzyl (4S,5S)-5-[(S)-1-(3-methylbutylcarbamoyl)pentylcarbamoyl]-1,3,2-dioxathiolane-4-carboxylate-2,2-dioxide

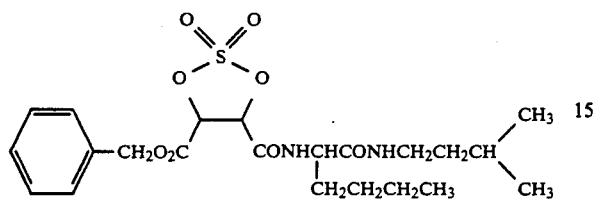

Following the same procedures as in Example 4, 169 mg of a target compound were prepared as white crystals from benzyl (2S,3S)-2,3-dihydroxy-3-[(S)-1-(3-methylbutylcarbamoyl)pentylcarbamoyl]propionate (205 mg) obtained in Example 25. NMR data of the target compound were as follows.

¹H—NMR (CDCl₃) δ ppm: 0.80-0.97 (9 H, m, —CH₃×3), 1.20-1.44 (6 H, m), 1.55-1.90 (3 H, m), 3.28 (2 H, m, —NHCH₂—), 4.37 (1 H, dd, J=7.5, 14.3 Hz, >CHCONH—), 5.32 (2 H, br s, —CH₂Ph), 5.47 (1 H, d, J=3.8 Hz), 5.56 (1 H, d, J=3.8 Hz), 5.84 (1 H, t, J=5.4 Hz, —CONHCH₂—), 7.18 (1 H, d, J=8.0 Hz, —NHCHCO—), 7.34-7.47 (5 H, m, arom)

SIMS m/z; 485 (M +1).

mp; 117.7°-118.7° C.

EXAMPLE 27

Benzyl (2S,3S]-2,3-dihydroxy-3-(S)-3-methyl-1-phenethylcarbamoylbutylcarbamoyl]propionate

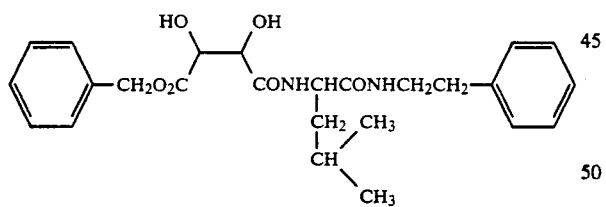

Following the same procedures as in Example 23, 143 mg of a target compound were prepared by condensing (1S,2S)-2-benzyloxycarbonyl-1,2-dihydroxyethanecarbonyl-L-leucine (161 mg) obtained in Reference Example 11 and phenethylamine (57 mg). NMR data of the target compound were as follows.

¹H—NMR (CDCl₃) δ ppm: 0.80-0.94 (6 H, m, —CH₃×2), 1.44-1.70 (3 H, m), 2.79 (2 H, t, J=7.4 Hz, —CH₂CH₂Ph), 3.33 (1 H, d, J=7.8 Hz), 3.52 (2 H, m, —NHCH₂—), 3.98 (1 H, d, J=7.8 Hz), 4.32-4.41 (1 H, m, >CHCONH—), 4.45 (1 H, dd, J=1.8, 7.8 Hz), 4.68 (1 H, dd, J=1.8, 7.8 Hz), 5.25 (2 H, br s, —CH₂Ph), 6.23 (1 H, t, J=6.9 Hz, —CONHCH₂—), 7.01 (1 H, d, J=8.9 HZ, —NHCHCO—), 7.12-7.40 (10 H, m, arom)

EXAMPLE 28

Benzyl (4S,5S)-5-[(S)-3-methyl-1-phenethylcarbamoylbutylcarbamoyl]-1,3,2-dioxathiolane-4-carboxylate-2,2-dioxide

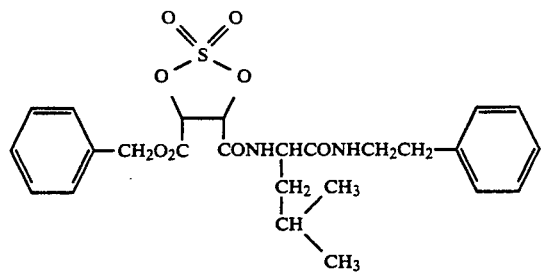

Following the same procedures as in Example 4, 82 mg of a target compound were prepared as white crystals from benzyl (2S,3S)-2,3-dihydroxy-3-[(S)-3-methyl-1-phenethylcarbamoylbutylcarbamoyl]propionate (109 mg) obtained in Example 27. NMR data, SIMS data, and a melting point of the target compound were as follows.

1H—NMR (CDCl₃) δ ppm: 0.81-0.98 (6 H, m, —CH₃×2), 1.47-1.70 (3H, m), 2 82 (2 H, d, J=6.8 Hz, —CH₂CH₂Ph), 3.56 (2 H, m, —NHCH₂—), 4.32 (1 H, m, >CHCONH—), 5.33 (2 H, br s, —CH₂Ph), 5.40 (1 H, d, J=3.7 Hz), 5.49 (1 H, d, J=3.7 Hz), 5.77 (1 H, br s, —CONHCH₂—), 6.82 (1 H, d, J=8.8 Hz, —NHCHCO—), 7.10-7.50 (10 H, m, arom)

SIMS m/z; 519 (M+1).

mp; 99.2°-101 0° C.

EXAMPLE 29

Benzyl (2S,3S)-2,3-dihydroxy-3-[(S)-3-methyl-1-phenylcarbamoylbutylcarbamoyl]propionate

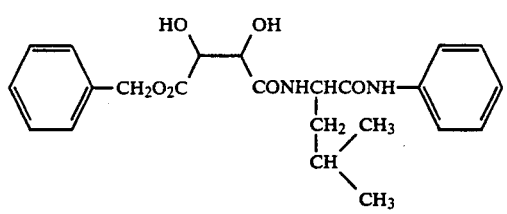

Following the same procedures as in Example 23, 93 mg of a target compound were obtained by condensing (1S,2S)-2-benzyloxycarbonyl-1,2-dihydroxyethanecarbonyl-L-leucine (200 mg) obtained in Reference Example 11 and aniline (59 mg). NMR data of the target compound were as follows.

¹H—NMR (CDCl₃) δ ppm: 0.80-1.01 (6 H, m, —CH₃×2), 1.57-1.82 (3 H, m), 3.66 (1 H, d, J=7.3 Hz), 4.52 (1 H, d, J=5.7 Hz), 4.61-4.82 (3 H, m), 5.12 (1 H, d, J=12.2 Hz, —CH₂Ph), 5.20 (1 H, d, J=12.2 Hz, —CH₂Ph), 6.97-7.56 (11 H, m, —CONHCH< and arom) 8.99 (1 H, br s, —CONHPh)

EXAMPLE 30

Benzyl (4S,5S]-5-[(S)-3-methyl-1-phenylcarbamoylbutylcarbamoyl]-1,3,2-dioxathiolane-4-carboxylate-2,2-dioxide

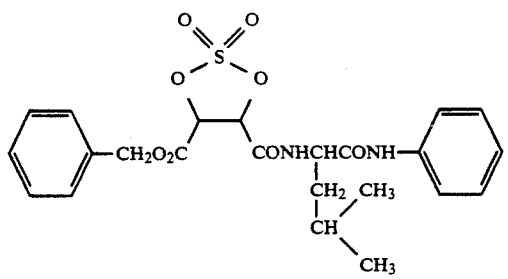

Following the same procedures as in Example 4, 17 mg of a target compound were prepared from benzyl (2S,3S)-2,3-dihydroxy-3-[(S)-3-methyl-1-phenylcarbamoylbutylcarbamoyl]propionate (25 mg) obtained in Example 29. NMR data of the compound were as follows.

$^1$H—NMR (CDCl$_3$) δ ppm: 0.83–1.08 (6 H, m, —CH$_3$×2), 1.52–1.81 (3 H, m), 4.59–4.72 (1 H, m), 5.33 (2 H, br s, —CH$_2$Ph), 5.50 (1 H, d, J=3.6 Hz), 5.54 (1 H, d, J=3.6 Hz), 7.20–7.59 (10 H, m, arom).

As has been described above in detail, 1,3,2-dioxathiolane oxide derivatives according to the present invention are novel compounds and can specifically and strongly inhibit thiol proteases without adversely affecting the activity of proteolytic enzymes such as trypsin, chymotrypsin, elastase, and leucineaminopeptidase. Therefore, these compounds can be used as a prophylactic or curing medicine against, e.g., myotonic dystrophy, inflammation, renal hypertension, cataracts, myocardial infarct, viral infectious diseases, malignant tumors, osteoporosis, and allergic diseases.

What is claimed is:

1. A 1,3,2-dioxathiolane oxide derivative represented by the following formula:

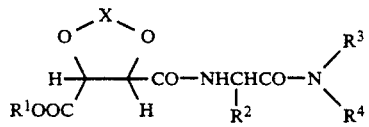 [I]

wherein

X represents —S(O)— or —S(O)$_2$—,

R$^1$ represents a hydrogen atom, an alkali metal atom, a benzyl group, or a lower alkyl group, R$^2$ represents a lower alkyl group or a lower alkyl group which is substituted with a methylthio group, or a benzyl group, and R$^3$ and R$^4$ may be the same or different and independently represent a hydrogen atom, an alkyl group having one to ten carbon atoms, a lower alkyl group substituted with a guanidyl group, a cycloalkyl group having 3 to 6 carbon atoms, a phenyl group, a benzyl group, or a phenethyl group, or R$^3$ and R$^4$ together form an alkylene group, or a pharmacologically acceptable salt thereof.

2. A 1,2-diol derivative represented by the following formula:

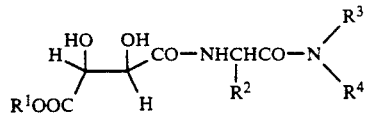 [II]

wherein R$^1$, R$^2$, R$^3$, and R$^4$ are each the same as defined in claim 1.

3. A 1,3-dioxolane derivative represented by the following formula:

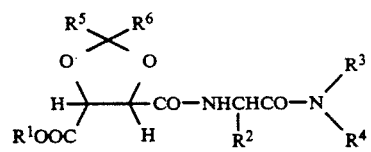 [III]

wherein

R$^1$, R$^2$, R$^3$, and R$^4$ are each the same as defined in claim 1, and

R$^5$ and R$^6$ may be the same or different and independently represent a hydrogen atom, a lower alkyl group, a nonsubstituted phenyl group, a lower alkoxy group, or a lower alkylamino group.

4. The 1,3,2-dioxathiolane oxide derivative of claim 1, wherein said R$^1$ and R$^2$ lower alkyl group each represents a straight-chain or branched alkyl group having one to five carbon atoms.

5. The 1,3,2-dioxathiolane oxide derivative of claim 4, wherein said R$^1$ and R$^2$ lower alkyl group each represents a straight-chain or branched alkyl group having one to four carbon atoms.

6. The 1,3,2-dioxathiolane oxide derivative of claim 4, wherein said R$^1$ and R$^2$ lower alkyl is each selected from the group consisting of a methyl group, an ethyl group, a propyl group, an isopropyl group, a butyl group, a sec-butyl group, and a tert-butyl group.

7. The 1,3,2-dioxathiolane oxide derivative of claim 1, wherein said R$^3$ and R$^4$ alkyl group each represents a member selected from the group consisting of a methyl group, an ethyl group, a propyl group, an isopropyl group, a butyl group, a sec-butyl group, a tert-butyl group, a pentyl group, an isopentyl group, a hexyl group, an isohexyl group, a heptyl group, an isoheptyl group, an octyl group, an isooctyl group, a nonyl group, an isononyl group, a decyl group, and an isodecyl group.

8. The 1,3,2-dioxathiolane oxide derivative of claim 1, wherein said alkylene group represents a divalent group derived from a saturated straight-chain aliphatic hydrocarbon having two to five carbon atoms.

9. The 1,2-diol derivative of claim 2, wherein said R$^1$ and R$^2$ lower alkyl group each represents a straight-chain or branched alkyl group having one to five carbon atoms.

10. The 1,2-diol derivative of claim 9, wherein said R$^1$ and R$^2$ lower alkyl group each represents a straight-chain or branched alkyl group having one to four carbon atoms.

11. The 1,2-diol derivative of claim 9, wherein said R$^1$ and R$^2$ lower alkyl group is each selected from the group consisting of a methyl group, an ethyl group, a propyl group, an isopropyl group, a butyl group, a sec-butyl group, and a tert-butyl group.

12. The 1,2-diol derivative of claim 2, wherein said R$^3$ and R$^4$ alkyl group each represents a member selected from the group consisting of a methyl group, an ethyl group, a propyl group, an isopropyl group, a butyl group, a sec-butyl group, a tert-butyl group, a pentyl group, an isopentyl group, a hexyl group, an isohexyl group, a heptyl group, an isoheptyl group, an octyl group, an isooctyl group, a nonyl group, an isononyl group, a decyl group, and an isodecyl group.

13. The 1,3-dioxolane derivative of claim 3, wherein said $R^1$ and $R^2$ lower alkyl group each represents a straight-chain or branched alkyl group having one to five carbon atoms.

14. The 1,3-dioxolane derivative of claim 13, wherein said $R^1$ and $R^2$ lower alkyl group each represents a straight-chain or branched alkyl group having one to four carbon atoms.

15. The 1,3-dioxolane derivative of claim 14, wherein said $R^1$ and $R^2$ lower alkyl group is each selected from the group consisting of a methyl group, an ethyl group, a propyl group, an isopropyl group, a butyl group, a sec-butyl group, and a tert-butyl group.

16. The 1,3-dioxolane derivative of claim 3, wherein said $R^1$ and $R^2$ alkyl group each represents a member selected from the group consisting of a methyl group, an ethyl group, a propyl group, an isopropyl group, a butyl group, a sec-butyl group, a tert-butyl group, a pentyl group, an isopentyl group, a hexyl group, an isohexyl group, a heptyl group, an isoheptyl group, an octyl group, an isooctyl group, a nonyl group, an isononyl group, a decyl group, and an isodecyl group.

17. The 1,3-dioxolane derivative of claim 1, wherein said salt is an acid salt with an inorganic acid or an organic acid.

18. The 1,3-dioxolane derivative of claim 3, wherein said inorganic acid is selected from the group consisting of hydrochloric acid, sulfuric acid, phosphoric acid, and hydrobromic acid, and said organic acid is selected from the group consisting of tartaric acid, maleic acid, fumaric acid, succinic acid, and sulfonic acid.

19. A medical composition, comprising said 1,3,2-dioxathiolane oxide derivative of pharmaceutically acceptable salt thereof of claim 1 in an amount sufficient to inhibit thiol protease in combination with at least one member selected from the group consisting of an excipient, a stabilizer, a preservative, and a buffer.

20. The composition of claim 19, in the form of a tablet, a capsule, a granule, a powder, a liquid, a suppository, and an ointment.

21. A 1,3,2-dioxathiolane oxide derivative selected from the group consisting of:
Ethyl (4S,5S)-[(S)-3-methyl-1-(3-methylbutylcarbamoyl)butylcarbamoyl]-1,3,2-dioxathiolane-4-carboxylate-2-oxide,
Ethyl (4S,5S)-[(S)-3-methyl-1-(3-methylbutylcarbamoyl)butylcarbamoyl]-1,3,2-dioxathiolane-4-carboxylate-2,2-dioxide,
Ethyl (4R,5R)-[(S)-3-methyl-1-(3-methylbutylcarbamoyl)butylcarbamoyl]-1,3,2-dioxathiolane-4-carboxylate-2-oxide,
Ethyl (4R,5R)-[(S)-3-methyl-1-(3-methylbutylcarbamoyl)butylcarbamoyl]-1,3,2-dioxathiolane-4-carboxylate-2,2-dioxide,
Benzyl (4S,5S)-5-[(S)-3-methyl-1-(3-methylbutylcarbamoyl)butylcarbamoyl]-1,3,2-dioxathiolane-4-carboxylate-2,2-dioxide,
(4S,5S)-5-[(S)-3-methyl-1-(3-methylbutylcarbamoyl)butylcarbamoyl]-1,3,2-dioxathiolane-4-carboxy-2,2-dioxide,
Ethyl (4S,5S)-[(S)-1-(N,N-dibutylcarbamoyl)-3-methylbutylcarbamoyl]-1,3,2-dioxathiolane-4-carboxylate-2,2-dioxide,
Ethyl (4S,5S)-5-[(S)-1-benzylcarbamoyl-3-methylbutylcarbamoyl]-1,3,2-dioxathiolane-4-carboxylate-2,2-dioxide,
Ethyl (4S,5S)-5-[(S)-3-methyl-1-(piperidine-1-yl-carbonyl)butylcarbamoyl]-1,3,2-dioxathiolane-4-carboxylate-2,2-dioxide,
Ethyl (4S,5S)-5-[(S)-1-decylcarbamoyl-3-methylbutylcarbamoyl]-1,3,2-dioxathiolane-4-carboxylate-2,2-dioxide,
Ethyl (4S,5S)-5-[(S)-1-cyclohexylcarbamoyl-3-methylbutylcarbamoyl]-1,3,2-dioxathiolane-4-carboxylate-2,2-dioxide,
Benzyl (4S,5S)-[(S)-1-(3-methylbutylcarbamoyl)-2-phenylethylcarbamoyl]-1,3,2-dioxathiolane-4-carboxylate-2,2-dioxide,
Benzyl (4S,5S)-5-[(S)-1-(3-methylbutylcarbamoyl)pentylcarbamoyl]-1,3,2-dioxathiolane-4-carboxylate-2,2-dioxide,
Benzyl (4S,5S)-5-[(S)-3-methyl-1-phenethylcarbamoylbutylcarbamoyl]-1,3,2-dioxathiolane-4-carboxylate-2,2-dioxide,
Benzyl (4S,5S)-5[(S)-3-methyl-1-phenylcarbamoylbutylcarbamoyl]-1,3,2-dioxathiolane-4-carboxylate-2,2-dioxide,
Ethyl (4S,5S)-5-[(S)-1-decylcarbamoyl-3-methylbutylcarbamoyl]-1,3,2-dioxathiolane-4-carboxylate-2-oxide,
Ethyl (4S,5S)-5-[(S)-1-cyclopropylcarbamoyl-3-methylbutylcarbamoyl]-1,3,2-dioxathiolane-4-carboxylate-2,2-dioxide,
Ethyl (4S,5S)-5-[(S)-1-cyclopentylcarbamoyl-3-methylbutylcarbamoyl]-1,3,2-dioxathiolane-4-carboxylate-2-oxide,
Ethyl (4S,5S)-5-[(S)-1-cyclopentylcarbamoyl-3-methylbutylcarbamoyl]-1,3,2-dioxathiolane-4-carboxylate-2,2-dioxide,
Ethyl (4S,5S)-5-[(S)-1-(4-guanidobutylcarbamoyl)-3-methylbutylcarbamoyl]-1,3,2-dioxathiolane-4-carboxylate-2,2-dioxide,
Ethyl (4S,5S)-5-[(S)-3-methyl-1-(N,N-dimethylcarbamoyl)butylcarbamoyl]-1,3,2-dioxathiolane-4-carboxylate-2,2-dioxide,
Ethyl (4S,5S)-5-[(S)-1-(N,N-diisopropylcarbamoyl)-3-methylbutylcarbamoyl]-1,3,2-dioxathiolane-4-carboxylate-2-oxide,
Ethyl (4S,5S)-5-[(S)-1-(N,N-diisopropylcarbamoyl)-3-methylbutylcarbamoyl]-1,3,2-dioxathiolane-4-carboxylate-2,2-dioxide,
Ethyl (4S,5S)-5-[(S)-3-methyl-1-(pyrrolidine-1-ylcarbonyl)butylcarbamoyl]-1,3,2-dioxathiolane-4-carboxylate-2,2-dioxide,
Ethyl (4S,5S)-5-[(S)-2-methyl-1-(3-methylbutylcarbamoyl)butylcarbamoyl]-1,3,2-dioxathiolane-4-carboxylate-2-oxide,
Ethyl (4S,5S)-S-[(S)-2-methyl-1-(3-methylbutylcarbamoyl)butylcarbamoyl]-1,3,2-dioxathiolane-4-carboxylate-2,2-dioxide,
Ethyl (4S,5S)-5-[(S)-1-(3-methylbutylcarbamoyl)methylthiopropylcarbamoyl]-1,3,2-dioxathiolane-4-carboxylate-2,2-dioxide,
(4S,5S)-5-[(S)-3-methyl-1-(3-methylbutylcarbamoyl)butylcarbamoyl]-1,3,2-dioxathiolane-4-carboxy-2-oxide, Potassium (4S,5S)-5-[(S)-3-methyl-1-(3-methylbutyl-carbamoyl)butylcarbamoyl]-1,3,2-dioxathiolane-4-carboxylate-2,2-dioxide, and Butyl (4S,5S)-5-[(S)-3-methyl-1-(3-methylbutylcarbamoyl)butylcarbamoyl]-1,3,2-dioxathiolane-4-carboxylate-2,2-dioxide.

22. A 1,2-diol derivative selected from the group consisting of

Ethyl (2S,3S)-2,3-dihydroxy-3-[(S)-3-methyl-1-(3-methylbutylcarbamoyl)butylcarbamoyl]propionate, Ethyl (2R,3R)-2,3-dihydroxy-3-[(S)-3-methyl-1-(3-methylbutylcarbamoyl)butylcarbamoyl]propionate, (2S,3S)-2,3-dihydroxy-3-[(S)-3-methyl-1-(3-methylbutylcarbamoyl)butylcarbamoyl]propionic acid, Benzyl (2S,3S)-2,3-dihydroxy-3-[(S)-3-methyl-1-(3-methylbutylcarbamoyl)butylcarbamoyl]propionate, Ethyl (2S,3S)-2,3-dihydroxy-3-[(S)-1-(N,N-dibutylcarbamoyl)-3-methylbutylcarbamoyl]propionate, Ethyl (2S,3S)-2,3-dihydroxy-3-[(S)-1-benzylcarbamoyl-3-methylbutylcarbamoyl]propionate, Ethyl (2S,3S)-2,3-dihydroxy-3-[(S)-3-methyl-1-(piperdine-1-ylcarbonyl)butylcarbamoyl]propionate, Ethyl (2S,3S)-2,3-dihydroxy-3-[(S)-1-decylcarbamoyl-3-methylbutylcarbamoyl]propionate, Ethyl (2S,3S)-2,3-dihydroxy-3-[(S)-1-cyclohexylcarbamoyl-3-methylbutylcarbamoyl]propionate, Benzyl (2S,3S)-2,3-dihydroxy-3-[(S)-1-(3-methylbutylcarbamoyl)-2-phenylethylcarbamoyl]propionate, Benzyl (2S,3S)-2,3-dihydroxy-3[(S)-1-(3-methylbutylcarbamoyl)pentylcarbamoyl]propionate, Benzyl (2S,3S)-2,3-dihydroxy-3[(S)-3-methyl-1-phenethylcarbamoylbutylcarbamoyl]propionate, and Benzyl (2S,3S)-2,3-dihydroxy-3[(S)-3-methyl-1-phenylcarbamoylbutylcarbamoyl]propionate.

23. A 1,3-dioxolane derivative selected from the group consisting of

Ethyl (4S,5S)-5-[(S)-3-methyl-1-(3-methylbutylcarbamoyl)butylcarbamoyl]-2-phenyl-1,3-dioxolane-4-carboxylate, and Ethyl (4R,5R)-5-[(S)-3-methyl-1-(3-methylbutylcarbamoyl)butylcarbamoyl]-2-phenyl-1,3-dioxolane-4-carboxylate.

* * * * *